(12) United States Patent
Sur et al.

(10) Patent No.: US 11,281,896 B2
(45) Date of Patent: Mar. 22, 2022

(54) PHYSICAL ACTIVITY QUANTIFICATION AND MONITORING

(71) Applicant: Smith & Nephew, Inc., Memphis, TN (US)

(72) Inventors: Sudipto Sur, San Diego, CA (US); Brett Juhas, San Diego, CA (US)

(73) Assignee: Smith & Nephew, Inc., Memphis, TN (US)

( * ) Notice: Subject to any disclaimer, the term of this patent is extended or adjusted under 35 U.S.C. 154(b) by 130 days.

(21) Appl. No.: 16/653,153

(22) Filed: Oct. 15, 2019

(65) Prior Publication Data

US 2020/0160044 A1 May 21, 2020

Related U.S. Application Data

(60) Provisional application No. 62/768,012, filed on Nov. 15, 2018.

(51) Int. Cl.
*G06K 9/00* (2006.01)
*G06T 7/521* (2017.01)

(52) U.S. Cl.
CPC .......... *G06K 9/00342* (2013.01); *G06T 7/521* (2017.01)

(58) Field of Classification Search
CPC ............................. G06K 9/00342; G06T 7/521
(Continued)

(56) References Cited

U.S. PATENT DOCUMENTS 8,761,437 B2   6/2014  Kirovski et al.
9,161,708 B2  10/2015  Elliott et al.
(Continued)

FOREIGN PATENT DOCUMENTS

CN   102693413 A   9/2012
CN   105453128 A   3/2016
(Continued)

OTHER PUBLICATIONS

Devanne, M. et al.. "3-D Human Action Recognition by Shape Analysis of Motion Trajectories on Rieemannian Manifold", IEEE Transactions on Cybernetics, Jul. 2015, pp. 1340-1352, vol. 45, No. 7.
(Continued)

*Primary Examiner* — Ayodeji O Ayotunde
(74) *Attorney, Agent, or Firm* — Kacvinsky Daisak Bluni PLLC

(57) ABSTRACT

Certain aspects provide a method of generating a physical activity model, including: receiving, via a motion capture device, motion data corresponding to a plurality of key states associated with a physical activity sequence; for each respective key state in the plurality of key states: determining a plurality of joint positions associated with the respective key state; determining a plurality of body segment positions associated with the respective key state based on the plurality of joint positions; determining a plurality of inter-state differentiation variables for the respective key state; determining one or more state characteristic metrics for the respective key state; and determining a classifier for the respective key state based on the one or more state characteristic metrics; and defining a physical activity model based on the one or more state characteristic metrics and the classifier associated with each key state.

21 Claims, 15 Drawing Sheets

(58) Field of Classification Search
USPC .......................................................... 382/103
See application file for complete search history.

(56) References Cited

U.S. PATENT DOCUMENTS

| | | | |
|---|---|---|---|
| 9,171,201 B2 | 10/2015 | Lake, II et al. | |
| 9,510,789 B2 | 12/2016 | Houmanfar et al. | |
| 9,826,923 B2 | 11/2017 | Houmanfar et al. | |
| 2011/0228976 A1 | 9/2011 | Fitzgibbon et al. | |
| 2012/0214594 A1* | 8/2012 | Kirovski | G06K 9/00355 463/36 |
| 2014/0228985 A1 | 8/2014 | Elliott et al. | |
| 2015/0317515 A1 | 11/2015 | Lake, II et al. | |
| 2017/0061817 A1 | 3/2017 | Mettler May | |
| 2018/0279916 A1* | 10/2018 | Folland | A61B 5/6804 |

FOREIGN PATENT DOCUMENTS

| | | |
|---|---|---|
| CN | 108463271 A | 8/2018 |
| EP | 2676242 A2 | 12/2013 |
| EP | 3005280 A1 | 4/2016 |
| EP | 3341093 A1 | 7/2018 |
| JP | 2014509011 A | 4/2014 |
| JP | 2016524929 A | 8/2016 |
| KR | 201400005233 A | 1/2014 |
| WO | 2012112402 A2 | 8/2012 |
| WO | 2014194337 A1 | 12/2014 |
| WO | 2017040242 A1 | 3/2017 |

OTHER PUBLICATIONS

Jose Perales, Francisco et al., "Articulated Motion and Deformable Objects", 8th International Conference, Jul. 16, 2014, pp. 1-205, AMDO 2014 Palma de Mallorca.

Bandouch, J. et al., "A Self-Training Approach for Visual Tracking and Recognition of Complex Human Activity Patterns", 2012, pp. 166-189, vol. 99.

Sanchez Gomez, P., International Search Report for PCT Application No. PCT/US2019/060637, dated Feb. 26, 2020, 6 pages.

* cited by examiner

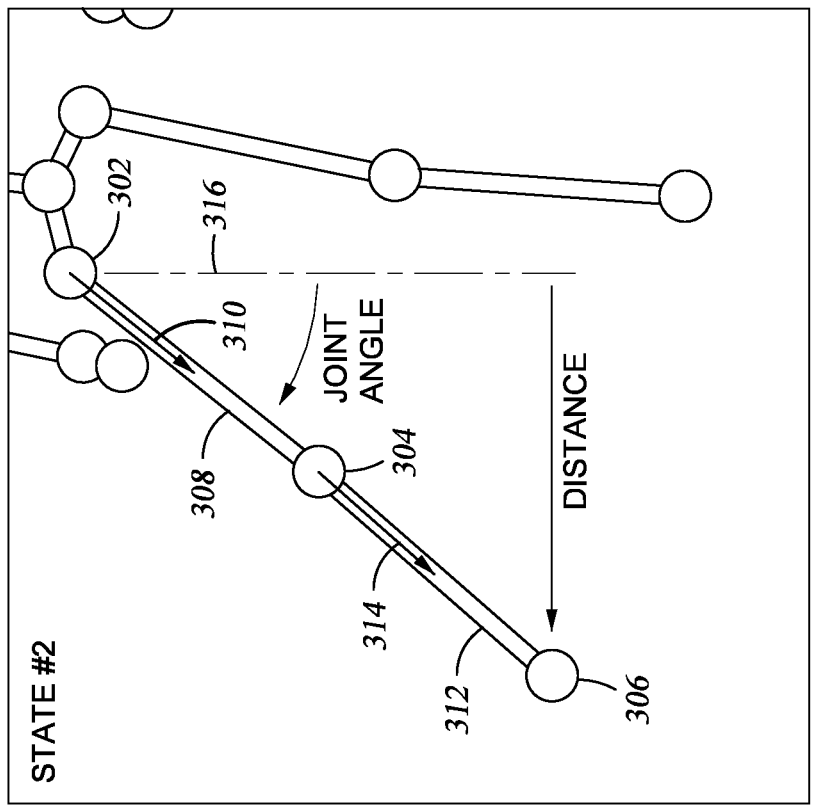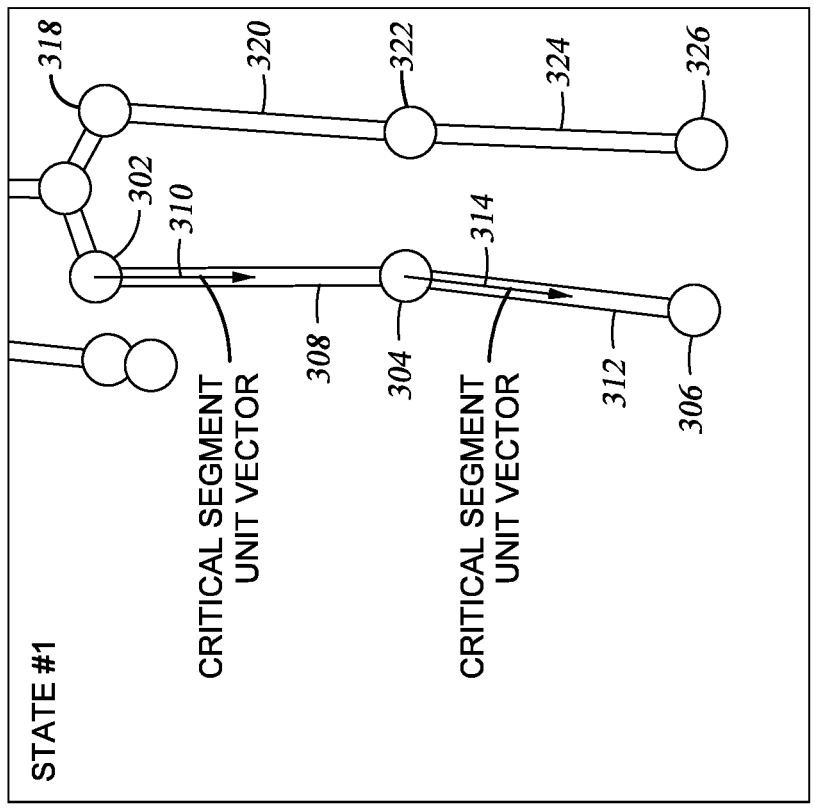
Fig. 3

| Exercise Tracking | Model Development | Data Analysis |

Exercise Creation

New | Edit

Select Exercise :

Hip Abduction Standing Left ▽

Select Exercise Version:

1 ▽

States = 2
State Sequence = 1 - 2 - 1
Metrics:

Training Data

- *File Count: 4*

Subject Name:

[ Record ]  [ Save ]

Model

[ Create ]  [ Re-Process ]  [ Save ]

Rep Tracking Metrics — *908*

State #1 ▽   *904*   *902*

| Selected | Strength | Metric Name |
|---|---|---|
| ☑ | 0.1251 | Left Thigh Roll |
| ☑ | 0.1199 | Left Shin Roll |
| ☐ | 0.1051 | Left Thigh |
| ☐ | 0.0970 | Left Shin |
| ☐ | 0.0299 | Right Thigh Roll |
| ☐ | 0.0232 | SpineBase-Pivot Roll |
| ☐ | 0.0198 | Right Thigh |
| ☐ | 0.0176 | Feet Placement |

*906*

PHYSICAL ACTIVITY QUANTIFICATION AND MONITORING

CROSS-REFERENCE TO RELATED APPLICATIONS

This application claims the benefit of U.S. Provisional Patent Application No. 62/768,012, filed on Nov. 15, 2018, which is incorporated herein by reference in its entirety.

INTRODUCTION

Aspects of the present disclosure relate to systems and methods for quantifying and monitoring physical activities based on motion data, and in particular, to generating physical activity models based on motion data captured from motion tracking systems.

In a physical rehabilitation setting, patients are often prescribed physical therapies, which may include specific, physical activities, such as exercises targeting specific movements of specific limbs and joints. Typically, a patient is given written instructions for when and how to perform the physical activities (e.g., a certain number of repetitions of a specific exercise every twelve hours). Historically, patients have also needed to go to a physical therapy clinic, or to have a clinician visit them at home, to monitor their physical therapy and to get feedback and coaching to maximize compliance with their physical therapy. Such on-site monitoring generally improves the efficacy of the physical therapy, for example, by ensuring that it is performed correctly and consistently. However, this conventional practice is time-consuming, expensive, and logistically challenging. Moreover in-clinic or in-home physical therapy coaching may not be available to those with limited mobility or means. While patients can perform prescribed physical therapies on their own without professional support, there is no guarantee that the patients will follow instructions and use proper form—which is critical to the efficacy of the prescribed physical therapies. In fact, unsupported physical therapy frequently leads to inferior patient outcomes, higher chances of re-injury, and the like.

Notably, the same issues faced in the physical therapy context are present in other contexts, such as physical fitness training for performance improvement rather than injury recovery, in coaching of athletes for various sports, and in any other context where the consistency and quality of body motions may improve a desired outcome.

Accordingly, what are needed are systems and methods for quantitatively defining physical activities, which allow for automated monitoring and feedback without the need for on-site personnel.

BRIEF SUMMARY

Certain embodiments provide a method of generating a physical activity model, comprising: receiving, via a motion capture device, motion data corresponding to a plurality of key states associated with a physical activity sequence; for each respective key state in the plurality of key states: determining a plurality of joint positions associated with the respective key state; determining a plurality of body segment positions associated with the respective key state based on the plurality of joint positions associated with the respective key state; and determining a plurality of inter-state differentiation variables for the respective key state based on one or more of: the plurality of joint positions associated with the respective key state; or the plurality of body segment positions associated with the respective key state; determining one or more state characteristic metrics for the respective key state based on the plurality of inter-state differentiation variables associated with the respective key state; and determining a classifier for the respective key state based on the one or more state characteristic metrics; and defining a physical activity model based on the one or more state characteristic metrics and the classifier associated with each key state.

Further embodiments provide a processing system, comprising: a non-transitory computer-readable medium comprising computer-executable instructions; and a processor configured to execute the computer-executable instructions and cause the processing system to perform a method of generating a physical activity model, the method comprising: receiving, via a motion capture device, motion data corresponding to a plurality of key states associated with a physical activity sequence; for each respective key state in the plurality of key states: determining a plurality of joint positions associated with the respective key state; and determining a plurality of body segment positions associated with the respective key state based on the plurality of joint positions associated with the respective key state; determining a plurality of inter-state differentiation variables for the respective key state based on one or more of: the plurality of joint positions associated with the respective key state; or the plurality of body segment positions associated with the respective key state; determining one or more state characteristic metrics for the respective key state based on the plurality of inter-state differentiation variables associated with the respective key state; and determining a classifier for the respective key state based on the one or more state characteristic metrics; and defining a physical activity model based on the one or more state characteristic metrics and the classifier associated with each key state.

Further embodiments provide a method for using a physical activity model, comprising: receiving motion data from a motion capture device; providing the received motion data to a physical activity model, wherein the physical activity model comprises: a plurality of classifiers, wherein each classifier of the plurality of classifiers is associated with a key state of a physical activity; and a plurality of state characteristic metrics, wherein each state characteristic metrics of the plurality of state characteristic metrics is associated with one or more of the plurality of classifiers; receiving, from the physical activity model, a plurality of scores, wherein each score of the plurality of scores is associated with one of the plurality of classifiers; and determining a key state is represented in the received motion data based on the plurality of scores.

Other embodiments include non-transitory computer-readable mediums comprising computer-executable instructions for performing the aforementioned processes as well as the additional processes described herein as well as processing systems configured to perform the aforementioned processes as well as the additional processes described herein.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIG. 3 depicts an example of determining candidate inter-state differentiation variables that may be used to distinguish between key states of a physical activity.

FIG. 9 depicts a portion of user interface in which various state characteristic metrics are displayed.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
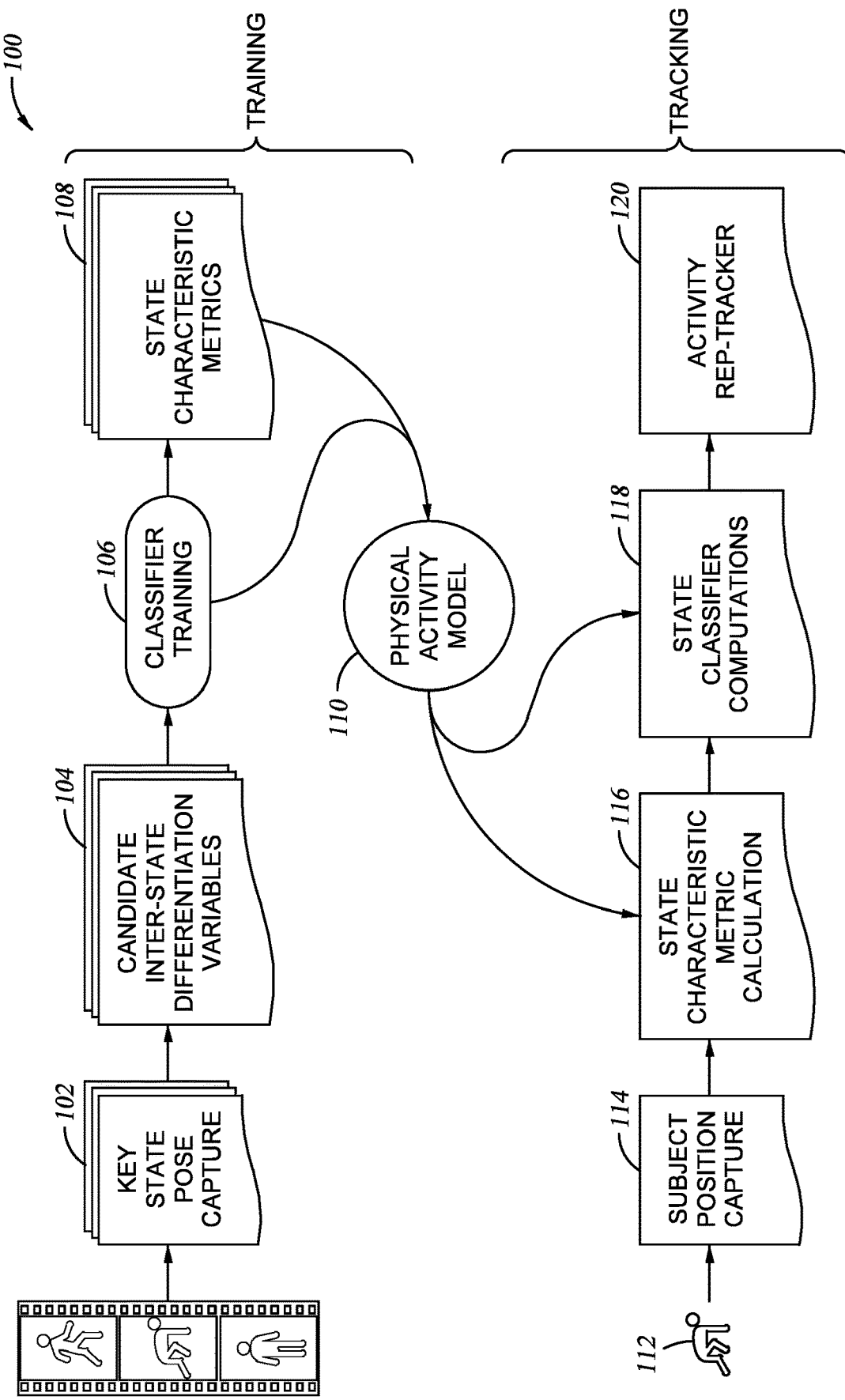
FIG. 1 depicts an example flow for creating and using a physical activity model.

Aspects of the present disclosure provide apparatuses, methods, processing systems, and computer readable mediums for quantitatively defining and monitoring physical activities based on captured motion data.

Generally, a physical activity may include a bodily activity that includes a temporal sequence of states of a subject's body. Physical activities may take many different forms. For example, a physical activity may comprise an exercise or other prescribed motion performed or practiced in order to develop, improve, or display a physical capability or skill.

A state, or activity state, associated with a physical activity may generally include a particular position, pose, or bearing of the subject's body, whether characteristic or assumed for a special purpose. One or more of the states in a sequence of states defining a physical activity may be considered a key state, which is a specific state that in-part defines the physical activity. Determination of specific key states is useful to ensure proper physical activity model formulation for state differentiation.

For example, the physical activity of sitting down may have a first key state of standing and a second key state of sitting. The states in between standing and sitting may not be considered "key" because they may not be important to defining the overall physical activity of sitting. Key states may be determined by experts, such as trainers, clinicians, doctors, or the like, or determined based on analyses of temporal sequences of states associated with a physical activity. For example, points of inflection during the motion path of a particular body segment or joint may indicate a key state of a particular physical activity.

In some cases, a physical activity may be further defined by temporal specifications, such as a need to move from one state to another within a specified time, or a need to hold one state for a specified time, to name just a few examples.

Each state in a physical activity state sequence may be defined with reference to individual segments or portions of a subject's body, such as the subject's head, neck, torso, arms, hands, fingers, legs, feet, bones, and others. Physical activities may be further defined by joints, which are generally connection points between two adjoining body segments that allow for some articulation of one segment in relation to another connected segment. In some cases, the individual segments and joints associated with a subject may be combined to form a digital body representation, such as a skeleton representation, or other more featured representation, such as an avatar.

Physical activity state sequences may be captured and digitized through a process of motion capture, motion monitoring, motion tracking, or the like, which all generally refer to a process for generating data regarding a subject's kinematic motion and static poses using a variety of electronic sensors. Generally, a motion tracking system may include hardware and software components configured to monitor a subject's physical activity (e.g., movements, exercises, etc.). In some embodiments, a motion capture device may include optical camera systems with image processing, marker based tracking systems with various marker (active, passive, semi-passive, modulated) and detector (optical, radio frequency) types, depth camera systems with object recognition algorithms, inertial measurement units, mechanical exoskeleton motion capture systems, or magnetic flux measurement systems, to name a few. One example of a motion tracking system is the KINECT® sensor and its associated pose detection software by MICROSOFT®.

States in a physical activity state sequence may be compared to generate state differentiation variables. For example, a plurality of candidate inter-state differentiation variables may be defined based on body segments and joints in order to identify or improve identification of differences between states, including key states, of a physical activity. In some embodiments, the plurality of candidate inter-state differentiation variables may be tested to determine a subset of inter-state differentiation variables that are most effective for identifying particular states, such as key states, in captured motion data. The selected subset inter-state differentiation variables may be referred to as state characteristic metrics, which are generally used by a physical activity model for identification and tracking of key states of a physical activity in motion data.

An ideal physical activity sequence may be defined, for example, by capturing motion data of a professional performing a physical activity in a prescribed manner and thereafter defining key states of the physical activity based on the captured motion data. As above, the key states may be defined manually, such as by a professional, or automatically, by analyzing the change in variables in captured motion data during performance of the ideal physical activity sequence. Further, in some implementations, key states can be numerically defined without a sample of collected motion capture data, such as by use of a skeletal data model.

Once a physical activity has been defined through quantification, as above, a physical activity model may be generated to determine (e.g., recognize or identify) states, such as key states, of the physical activity in captured motion data. Further, the physical activity model may compare the determined states with states of an ideal physical activity state sequence to "score" a subject's performance of the physical activity and/or to provide live feedback to the subject on the quality of the performance of the physical activity. This enables, in effect, live monitoring and feedback to a subject without the need for an on-site professional.

In some embodiments, a physical activity model comprises one or more classifiers that are configured to determine probabilities that a particular state is represented in captured motion data. Further, for each classifier of the physical activity model, a classifier confidence may be determined as a quantitative assessment corresponding to the classifier's performance in determining a correct state, classification, or category of captured motion data. Determination of particular states via the physical activity model may further lead to determination that a defined physical activity, which comprises some or all of the determined states, is represented in the captured motion data.

In some embodiments, a physical activity model further comprises one or more state characteristic metrics, as described above. The combination of classifiers and state characteristic metrics enables a single physical activity model to generate predictions regarding a plurality of defined states and physical activities in captured motion data.

Capturing Motion Data for Quantifying and Monitoring Physical Activities

In embodiments described herein, a physical activity monitoring system is configured to capture motion data regarding a subject's physical activity (e.g., performing a specific movement or sequence of movements as a part of an exercise), quantitatively compare the captured motion data against one or more defined physical activity models, and to provide real-time monitoring and feedback regarding the subject's physical activity. Notably, this may be done without the need for an on-site professional, such as a doctor, clinician, coach, trainer, or the like. Even without a professional on-site, embodiments described herein enable an off-site professional to, for example, review captured motion data, review monitoring data generated by one or more physical activity models, and review system generated feedback based on the monitoring data, to further improve feedback to the subject.

FIG. 1 depicts an example flow 100 for generating and using a physical activity model.

Flow 100 begins at step 102 with capturing motion data associated with key states of a physical activity. As above, key states may include specific body poses as well as specific temporal aspects of time in a pose as well as time in transition between poses.

In some embodiments, the key states may be defined by a professional and performed by a professional in order to quantitatively define the physical activity through captured motion data. In other embodiments, the key states may be determined automatically based on captured motion data, such as by identifying pauses, transitional sequences, or other indicators that one key state is transitioning to another key state.

In one example, in a rehabilitation context, a trainer (e.g., an expert practitioner, possibly a clinician) may predefine a sequence of key states, including temporal characteristics, and then enact them in front of a motion capture device. The motion capture device records the trainer's joint positions as they perform the activity. Thus, key states can be selected from a continuous execution of states of the activity without having the trainer hold a pose statically. In some embodiments, key states may be calculated based on a sequence of motion data in which the particular activity is repeated one or more times.

In some embodiments, the motion data captured by a motion capture system may be used to determine coordinates of a plurality of joint positions, from which body segments (e.g., limbs) can be determined to create a skeleton model or reconstruction of the trainer's motion during performance of the physical activity. In some embodiments, each body segment is defined as a length between distinguishing joints, and a unit vector may further be defined which gives the orientation of the body segment in a coordinate frame. In some embodiments, joint angles may also be calculated based on comparing the unit vectors of adjoining body segments vectors using vector mathematics.

Herein, absolute and relative joint positions are described as one way of tracking states of a subject's motions. However, the methods described herein are compatible with any mathematical representation of a state, including body segments, joint positions, and other body characteristics. Further, states may be represented by various methods, or combinations of methods, including: limb orientations, body spread, kinematic models of the body using rotation matrices or quaternions, body silhouette, body 3D point cloud spatial distribution metrics, parametric approaches, like the Sum of Gaussians (SoG) representation, and others. In other words, it is not necessary that a state be represented only as a set of joint positions.

In some embodiments, a subject's joint positions are derived using mathematical operations based on tracking data that does not directly provide joint positions. For example, a 3D point cloud system may not inherently provide joint positions, but machine learning approaches may be used to get the joint positions from the 3D point cloud. Similarly, marker based systems may not always have markers at the joints, but may use kinematic models of the body to figure out the joint positions given the locations of the sensors.

In certain situations, it may be advantageous to record training data (at step 102) from multiple subjects and/or using multiple tracking methodologies or devices. Differences can be found in the key states for subjects of varying size and shape and depending on the motion capture device used. Diversifying the training data may beneficially provide wider ranges of acceptable values for pose variables used for model formulation, and may thus result in more robust tracking performance for varying subjects. FIGS. 7, 8, 10, 11, and 12, below, depict an example of capturing motion data with two different motion capture devices simultaneously.

At step 104, one or more candidate inter-state differentiation variables are determined based on the key state motion data captured in step 102.

In one embodiment, at each key state in the temporal sequence of states associated with a physical activity, a set of candidate inter-state differentiation variables can be generated from quantified variables, such as joint angles, body segment unit vector orientations, and distances between specific joints, to name a few examples.

At step 106, one or more classifiers may be trained based on the one or more candidate inter-state differentiation variables.

In one embodiment, classifiers may be trained to analyze all candidate inter-state differentiation variables generated in step 104. Approaches for training the classifiers may include, for example, linear and non-linear regression techniques, supervised machine learning techniques, curve fitting, and clustering techniques, such as Gaussian Mixture Modeling (GMM) and k-means, to name a few.

During training of the classifiers, the values of each candidate inter-state differentiation variable at a given state may be compared to a combination of its values from all other states in the physical activity. In one embodiment, a classifier associated with each individual key state may be trained to produce a predicted classification by comparing itself to the combination of all other key states in the activity sequence. Thus, the classifiers may provide a continuous quantitative measure of the level of classification confidence, which may be used to determine key state achievement during tracking of a subject's motion.

In some embodiments, the statistical significance of each respective candidate inter-state differentiation variable is assessed using, for example, classifier outcomes and information regarding the relative change in the respective candidate inter-state differentiation variable value between states. In some embodiments, a subset of state characteristic metrics may be chosen (step 108) and retained in physical activity model 110 based on the significance analysis of each inter-state differentiation variable. The reduction of inter-state differentiation variables based on the significance analysis may beneficially reduce the computational resource needs associated with a physical activity model and therefore enable the physical activity model to run on lower power devices, such as portable electronic devices. However, the full set of inter-state differentiation variables may be used as state characteristic metrics if, for example, computational efficiency is not a consideration and if each inter-state differentiation variable is a statistically significant discriminator of different states.

Note that while classifiers are described in this example, other types of mathematical methods, such as those described above, can be utilized and designed to perform similar functionality.

A result of classifier training in step 106 is the identification of one or more state characteristic metrics at step 108. In this example, the state characteristic metrics are configured to be used as part of physical activity model 110 in conjunction with the trained classifiers in order to identify key states in motion data, such as in step 114. Notably, identifying key states in motion data may be based on a likelihood or probability calculation that the key state exists in the motion data. In some cases, a likelihood measure may be compared to a threshold to determine whether or not the key state is in the motion data. The description with respect to FIG. 4, below, provides additional detail regarding physical activity model generation.

Once physical activity model 110 is generated, such as by trained classifiers and state characteristic metrics, it may be used to track another subject's motion, to identify key states in that motion, and to quantify the performance of an observed physical activity (e.g., by reference to its key states) against an ideal physical activity state sequence, such as might be determined in steps 102-108. For example, physical activity model 110 may be used to monitor a patient 112 undertaking physical therapy at home.

For example, subject 112 may perform a prescribed physical activity in front of a motion capture device so that motion capture data is collected at step 114. The motion capture data is then used to calculate the state characteristic metrics (defined in step 108) at step 116 and one or more state classification estimates are produced by physical activity model 110 at step 118 via the trained classifiers. In some embodiments, classifier outcomes may be a probabilistic value representing physical activity model 110's confidence that a subject (e.g., patient 112 in this example) is currently performing the key state associated with each specific classifier.

The output of each classifier may be monitored throughout the continuous motion of a physical activity (e.g., of patient 112) and the peak probability values may be recorded. Further, as patient 112 moves through the sequence of states, the probability of each sequential state is checked against a threshold value. If the peak probabilistic values of each state are above this threshold, then it may be determined that the subject has completed a successful repetition of the prescribed exercise, and a repetition tracker may be updated at step 120. In some embodiments, the threshold value is predetermined, while in others, it may be dynamically computed. For example, the threshold value may be changed over time as the number of repetitions increases, or as the training regimen proceeds. Further, the threshold value may respond dynamically to the patient's performance so that it increases as a patient gets better or more consistent with its motions, or alternatively decreases if a patient is underperforming. These are just a few examples.

Notably, while exercises are used in the description of FIG. 1 and throughout as one example context, the methods described herein are applicable to any sort of physical activity. This includes biomechanical analysis of physical activity training, fitness regimens, and sport science research, such as training proper form or detection of critical movements. The methods described herein also may be used for clinical sciences, such as the analysis of posture, balance, gait, and motor control. Further, the methods described herein can be used for gesture/pose recognition and detection in virtual reality, gaming applications, robotics, manufacturing applications, and ergonomic studies. Further yet, the state-identification models described herein can also be applied in psychological studies for analysis on behavioral and physical response.

Flow 100 depicted in FIG. 1 presents many advantages over conventional systems and methods. For example, in flow 100, a specific set of classifiers, suited for a specific end task requirement, can be used for modeling activities without any change to the methodology presented. For example, if likelihood estimates of state classification are desired, statistical probabilistic models can be implemented to output a level of confidence while tracking an activity. Further, various classifiers can provide additional information regarding repetition tracking and overall performance of the subject.

Further, the physical activity models described herein can produce a continuous valued output, which can be used to track progression between states. This can provide subjects with live feedback regarding their activity progression and can be used as a guide to determine how far they must move to achieve the desired state pose.

The physical activity model outcomes may further be used to provide a prediction of risk and allow for cautionary feedback to prevent potential injury during an activity. In this way, the live physical activity model feedback may reduce the risk of over extension of monitored body segments and joint angles. A subject may be more likely to stop their motion once the intended state has been achieved and not over-exert themselves when live feedback is provided.

Further, the physical activity models described herein may be trained using a collection of data from varying subjects and varying devices to produce more robust monitoring results.

The identification of state characteristic metrics, as described herein, can be automated based on the statistical significance of each candidate inter-state differentiation variable. This overcomes the laborious task of manual identification of metrics in conventional methods.

Further, the physical activity models described herein can be automatically formulated using statistically derived relationships between states. Conventional methods have relied on more heuristic approaches utilizing discrete state-identification thresholds set manually based on empirical observations of a model demonstrator. The probabilistic classifier approach described herein may further remove potential bias of the activity model creator and produce a more statistically significant activity tracking methodology.

Further, physical activity models described herein benefit from their direct derivation from an actual full performance of a recorded activity. Physical activity model generation from real activity is significantly faster than heuristic approaches, which necessitate a trial and error approach during model development.

Further, the physical activity models described herein are easily tunable if slight revisions need to be made. For example, model parameterization can be performed, and the model's classifier formulas can be scaled to track activities with varying ranges of motion using the same training dataset. Further, during model formulation, a user may refine the list of state characteristic metrics to place more emphasis on tracking body segments of greater interest, such as depicted in FIG. 9. Further, as above, the threshold values of achieving key states may be dynamically changed over time in order to increase the strictness of exercise following as, for example, a rehabilitation regimen progresses, or as measured performance improves.

Though FIG. 1 depicts one example implementation, there are various ways of implementing the methodology described herein.

For example, a methodology in which a professional or other user explicitly demonstrates each key state is not required. Alternatively key states may be algorithmically determined from an analysis of the motion capture data.

As another example, physical activity models may also be used to detect erroneous positions that a subject should avoid during an activity sequence. In this regard, a physical activity model can be trained using motion data from a recorded erroneous pose, and formulated to identify when a subject has achieved such an undesirable position. These poses may include positions that could potentially result in injury or are engaging incorrect body regions.

As another example, the physical activity models described herein can be used for patient screening. For example, patients with issues of limited range of motion or inflexibility of certain joints associated with common ailments may perform physical activities in a distinguishable matter. Identification models may be formulated based on training data from varying types of subjects to detect certain conditions a patient may exhibit.

Further, the physical activity models described herein may be configured to track activity progression and compliance throughout the course of an activity set. A continuous valued model output may be used to determine if a subject is truly completing the full range of motion required for a prescribed physical activity. To this end, the subject's progression over the course of the physical activity may be monitored and ultimately used to make alterations to the prescribed activity.

As described above, formulation of physical activity models may generally require quantified information regarding key states. This data many come from varying sources or methods other than an optical-based motion capture source. A motion capture device may include optical camera systems with image processing, marker based tracking systems with various marker (active, passive, semi-passive, modulated) and detector (optical, radio frequency) types, depth camera systems with object recognition algorithms, inertial measurement units (IMUs), mechanical exoskeleton motion capture systems, or magnetic flux measurement systems or combinations of those system. Other potential sources include, but are not limited to, data extracted processing methods that compare sequential frames of data to determine differences. Depth cameras and/or point cloud mapping can also be used to extract information on varying states.

In some embodiments, physical activity models can be formulated from data expressed in various other coordinate spaces rather than the three-dimensional (3D) space generally described herein. For example, two-dimensional (2D) data could be extracted from image processing techniques, or 3D motion capture devices may project captured motion data onto a 2D plane.

While the physical activity models may be time-invariant in the examples described herein, they are nevertheless fully capable of tracking and comparing physical activity sequence timing. In some embodiments, ideal timing can be extracted from the training data to determine the desired rate of transition between states. These transition periods between states can be identified using the state classifiers and their associated probabilistic outputs. With discrete boundaries established between states and transition zones, time information can be recorded and binned into associated state/transition regions. Subject timing between-states, and during states, can be compared to that from the idealized motion recorded during model training.

Various statistical methods and classifiers can be applied for state-differentiation. These include, but are not limited to, logistic regression, Gaussian mixture models, Bayes classifiers, k-means clustering, artificial neural networks, decision tree classifiers, random forest regression, gradient tree boosting, and support vector machines.

State detection, as described above, may be formulated by comparing each state to the combination of all other states in the activity sequence. Many other variations of state comparison are also effective for physical activity model formulation. For example, multinomial regression techniques can be implemented for physical activity sequences with many state-positions within the sequence. Inter-state differentiation variables from each state can be compared to all other individual states, thus producing classifiers comparing all possible two-item combinations of states. Outputs of these 1 vs. 1 type classifiers can be combined during state-tracking to produce an estimated classification. States may also be compared only to other states that are contiguous in the activity sequence. Another effective method would be to compare all states to solely the initial state, and the resulting model results can be combined to produce state estimates during tracking.

Example Physical Activity State Sequence

As above, a physical activity may be defined as a sequence of key states a subject performs throughout one full cycle of the physical activity. Expressing a full sequence of states in a physical activity using a subset of "key states" from the full sequence allows for a time-invariant definition of the physical activity, which is also computationally more efficient. Given the kinematics of an articulated human skeleton, an appropriately chosen subset does not reduce the fidelity or quality of the exercise definition.

Figure 2:
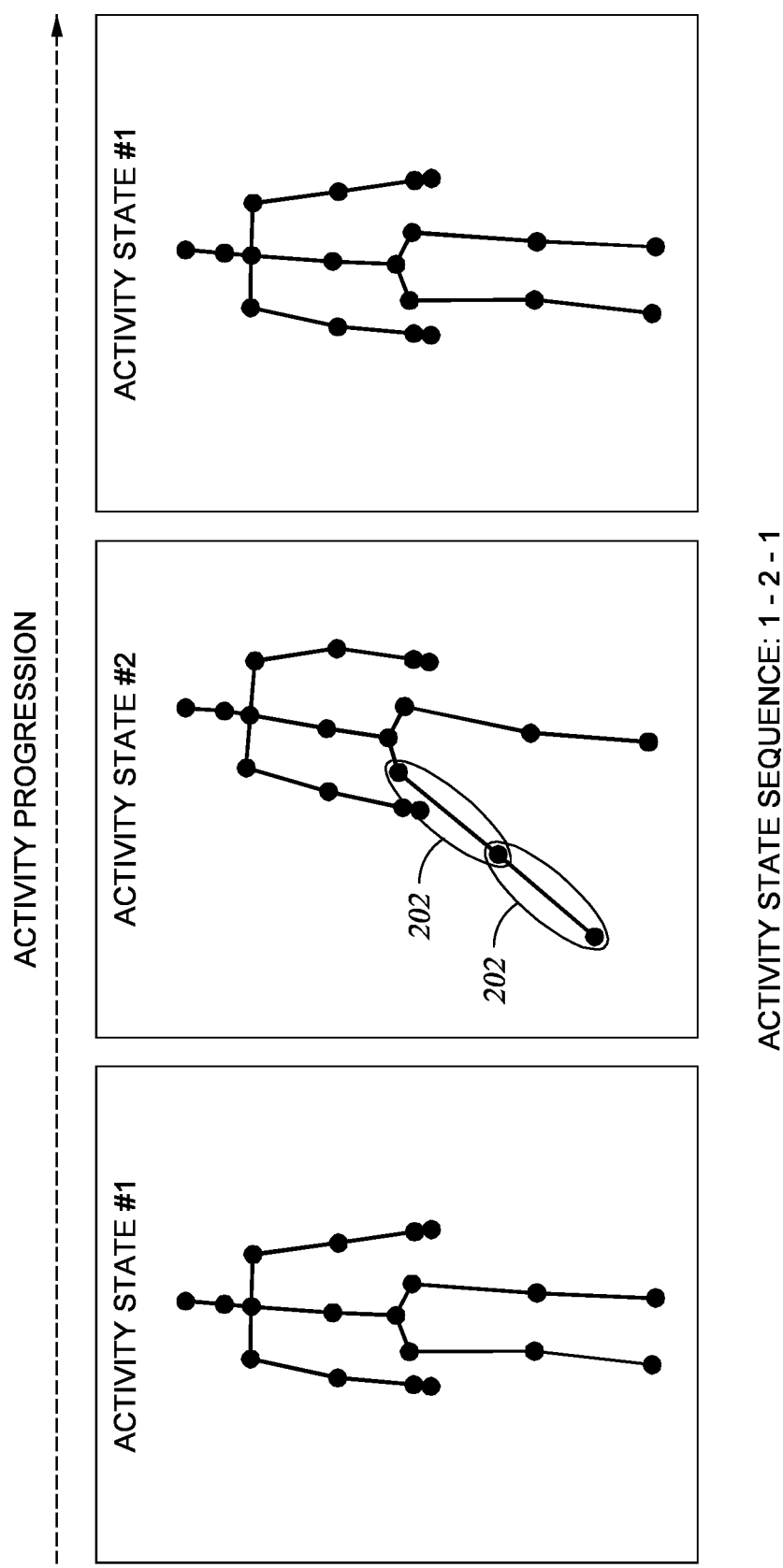
FIG. 2 depicts example output from a motion capture system showing the difference between two physical activity states.

FIG. 2 depicts example visualization from a motion capture system showing the difference between two physical activity states (poses in this example) during a physical activity sequence that progresses from State 1 to State 2 and back again to State 1. Notably, States 1 and 2 may be key states in a physical activity sequence.

In this example, the subject is standing upright in State 1 and is then extending one leg outward without a bend at the knee in State 2. Thus, in this example, it is evident that a subset of available body segments 202 can be used to distinguish between States 1 and 2.

The difference between each identified body segment and joint between States 1 and 2 may form a set of candidate inter-state differentiation variables as described further with respect to FIG. 3.

Example Candidate Inter-State Differentiation Variables

FIG. 3 depicts an example of determining candidate inter-state differentiation variables that may be used to distinguish between key states of a physical activity sequence.

As depicted in FIG. 3, it is possible to determine many candidate inter-state differentiation variables based on a relatively small number of joints and body segments. For example, here candidate inter-state differentiation variables may include: the angle of joints 302 and 318 from a reference, such as plane 316; the distance of joints 304, 306, 322, and 326, from a reference, such as a point or plane 316; unit vector orientations (e.g., 310 and 314) associated with body segments, such as 308, 312, 320, and 324; and others.

Focusing on State 2, it is clear there exists a subset of the candidate inter-state differentiation variables most relevant to identifying State 2 as compared to State 1. In this example, the angle of joints 302 from reference plane 316; the distance of joints 304 and 306 from reference plane 316; and unit vector orientations 310 and 314 associated with body segments 308 and 312 are most determinative of State 2 as they have changed the most between State 1 and State 2.

Notably, tracking a subset of states (e.g., key states), such as State 1 and State 2 in this example, rather than every possible state in a physical activity motion sequence, allows for calibrating or tuning the stringency with which a particular physical activity requirement is followed. For example, here slight changes in body segments 320 and 324 would not be considered when determining between State 1 and State 2. Beneficially, this allows subjects to deviate to a configurable degree from an ideal physical activity state sequence during transitions between states if so desired. To refine tracking, additional key states can be added to the activity to constrain the motion further.

Example Physical Activity Model Definition Based on Key States

Figure 4:
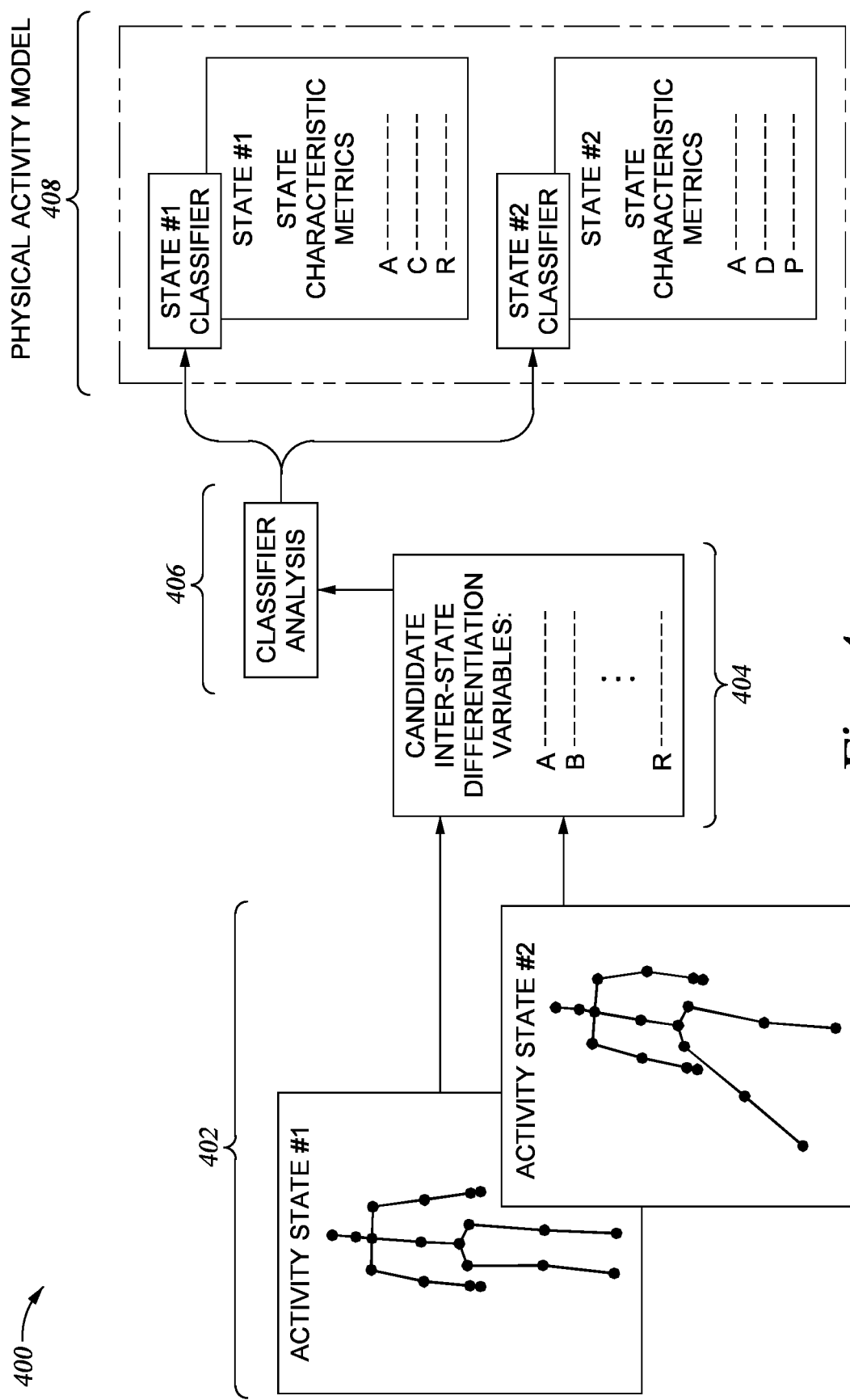
FIG. 4 depicts an example of training a physical activity model based on a plurality of key states

FIG. 4 depicts an example flow 400 for defining a physical activity model based on a plurality of key states. In particular, in this example, the activity states 402 from FIGS. 2 and 3 are used as example key states for training physical activity model 408.

As discussed above with respect to FIG. 3, a plurality of candidate inter-state differentiation variables 404 may be determined based on trackable aspects identified in motion capture data, such as trackable body segments and joint locations in States 1 and 2.

The candidate inter-state differentiation variables 404 may be analyzed at 406 using classification methods, such as those described above, to identify a subset of inter-state differentiation variables that are most effective at distinguishing between States 1 and 2 (402). In this example, statistically significant inter-state differentiation variables identified for each key state are referred to as state characteristic metrics, and finalized classifiers are formulated using the state metrics associated with each key state, as shown with respect to physical activity model 408.

In particular, in this example, candidate inter-state differentiation variables 404 included variables {A, . . . , Z}, whereas the resulting state characteristic metrics for State 1, based on the classifier analysis at 406, are {A, C, R}. Similarly, the resulting state characteristic metrics for State 2, based on the classifier analysis at 406, are {A, D, P}. As is the case in this example, selected inter-state differentiation variables may be included as state characteristic metrics for more than one key state (here A is included in each), though in other examples, each key state may have a unique set of state characteristic metrics.

Further in this example, once the characteristic metrics have been determined, finalized versions of classifiers (e.g., State 1 Classifier and State 2 Classifier in physical activity model 408) are created to monitor when each state has been achieved by the subject being monitored.

As mentioned above, training data regarding States 1 and 2 may be collected from sets of subjects performing the physical activity, and specific training data may be identified (e.g., tagged) as associated with each key state. When the training data comes from a set of subjects, the candidate inter-state differentiation variables may be calculated for each subject, at each state, and then pooled together. Then, classifiers compare the inter-state differentiation variable values for the varying key states in the physical activity to determine which inter-state differentiation variables provide significant information for state detection and classification. Capturing training motion data from varying subjects may improve the robustness of physical activity models such that they are capable of tracking a wider variety of subjects, such as subjects of varying size and body composition.

Figure 5:
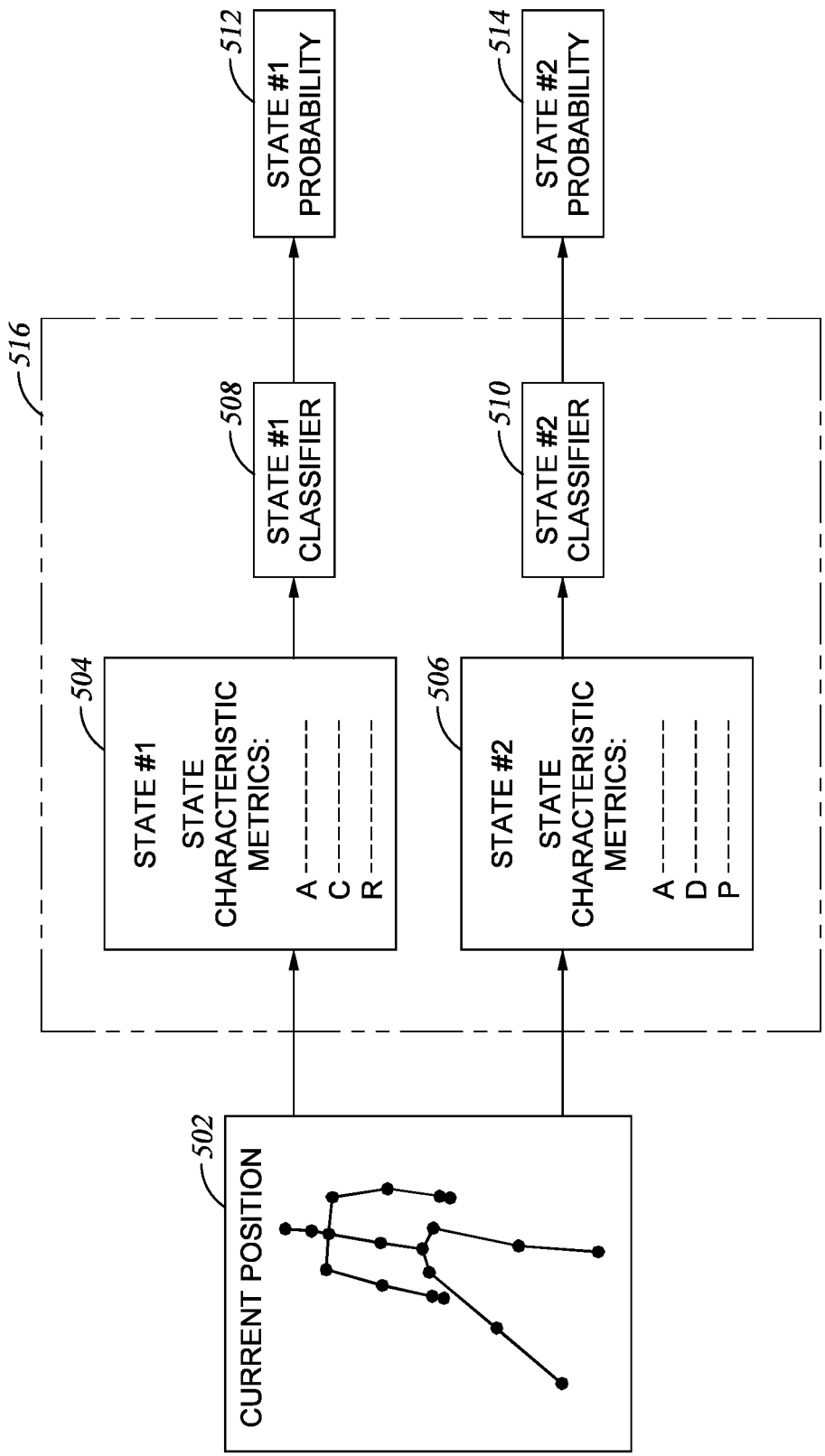
FIG. 5 depicts an example of determining physical activity state probabilities using a physical activity model.

Example Determination of Physical Activity State Probabilities Based on Captured Motion Data FIG. 5 depicts an example of determining state (e.g., key state) probabilities using a physical activity model 518 based on motion data, such as may be captured by a motion tracking system.

In the example depicted in FIG. 5, a subject's current position 502 is monitored by a motion tracking system. The motion data generated by the motion tracking system may include data regarding various tracked aspects of the subject's body, such as body segments and joints.

Motion data associated with specific state characteristic metrics are provided to each state-specific set of state characteristic metrics, such as 504 and 506. The state characteristic metric data for each state is then used by each state's classifier, such as 508 and 510, to produce probabilistic classifier confidence outcomes for each state, such as 512 and 514.

As the subject moves through a physical activity motion sequence, classifier outputs (e.g., state probabilities 512 and 514) are tracked and compared to state-achievement threshold values.

Further, in some embodiments, the order in which state poses are achieved may be monitored and compared to a sequence of key states defined by an ideal physical activity state sequence in order to determine a number of successful repetitions of a physical activity. An example of this is described below with respect to FIG. 12.

Figure 6:
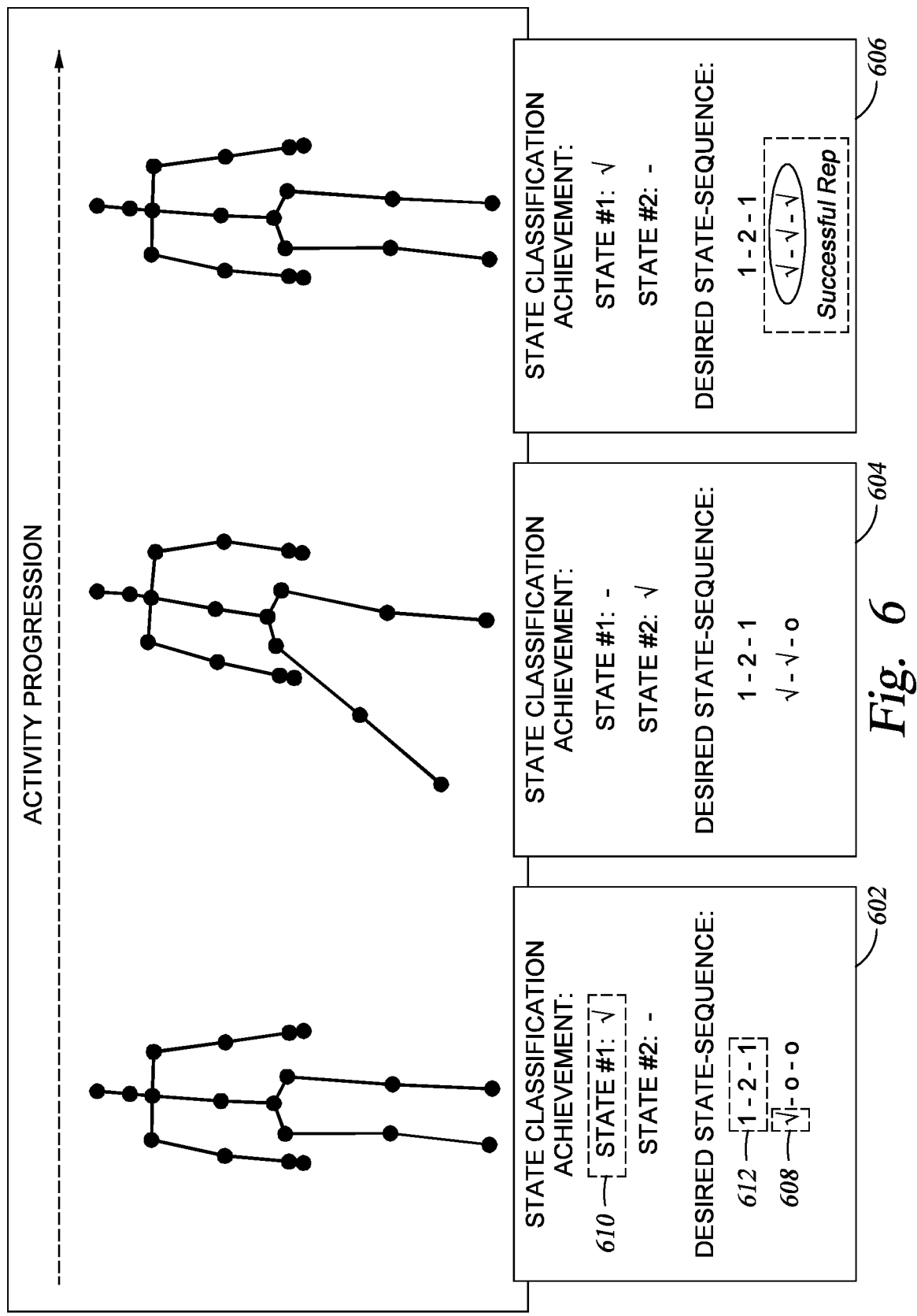
FIG. 6 depicts an example of tracking a defined physical activity state sequence.

Example Activity State Achievement and Activity State Sequence Repetition Counting FIG. 6 depicts an example of tracking a physical activity state sequence, such as an ideal physical activity state sequence.

Box 602 includes an indication 610 that a physical activity model has determined that State 1 has been achieved based on, for example, one or more state characteristic metrics and one or more state-specific classifiers associated with State 1. Further in box 602, there is an indication 608 that the subject has now achieved the first state in a desired state sequence 612 that is defined in this example as a progression from State 1 to State 2 and then back to State 1.

Similarly, as depicted in box 604, the physical activity model has determined that State 2 has been achieved based on, for example, one or more state characteristic metrics and one or more state-specific classifiers associated with State 2. Further in box 604, there is an indication that the subject has now achieved the first state and the second state in the desired state sequence 612.

Finally, in box 606, the physical activity model has determined that State 1 has been achieved once again. Further in box 606, there is an indication 614 that the subject has now achieved all of the states in the desired state sequence 612, and that a successful repetition has been counted.

Figure 7:
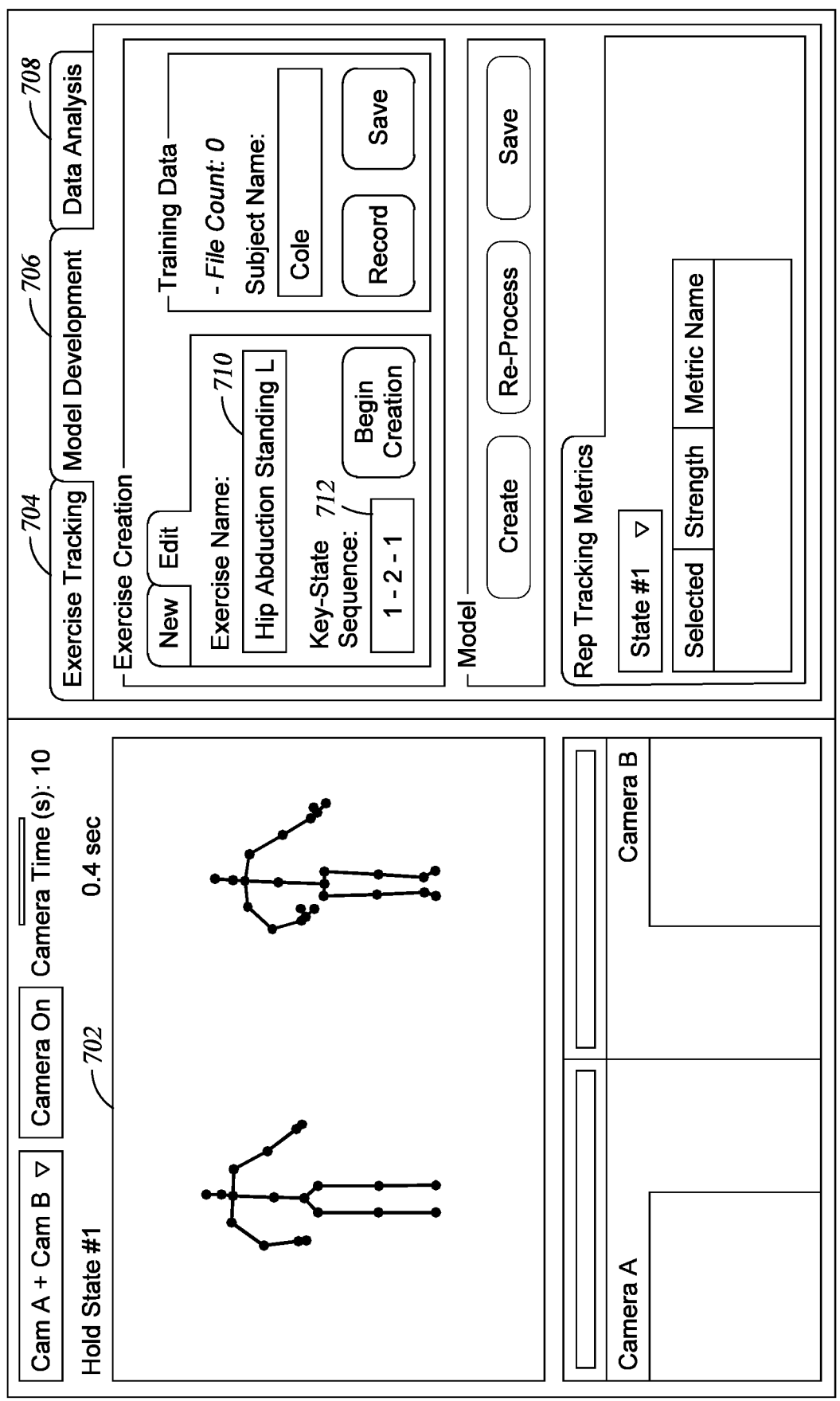
FIG. 7 depicts an example user interface for recording training data for physical activity model development.

Example Graphical User Interfaces for Recording Training Data for a Physical Activity Model FIG. 7 depicts an example user interface 700 for recording training data for physical activity model development.

In particular, user interface 700 includes a portion 702 that shows live tracking data, which in this example includes captured motion data from two motion tracking systems simultaneously. As described above, capturing motion data from multiple motion tracking systems may improve the resulting physical activity model by providing more diverse training data for classifier training (e.g., as in step 106 in FIG. 1). Further, motion data from different motion capture systems may be used to generate physical activity models that are specific or optimized to the motion capture system.

User interface 700 further includes a plurality of mode selection tabs, including an exercise tracking mode tab 704, a model development tab 706, and a data analysis tab 708. In this example, model development tab 706 is selected and information regarding the physical activity is displayed. For example, here the name 710 of the physical activity being modeled is a "Hip Abduction Standing Left", and this physical activity is being modeled with a key state sequence 712 of 1-2-1. Further, as depicted in portion 702, a subject is currently demonstrating the State 1 pose. In some embodiments, the first state (here, State 1) in a defined physical activity state sequence may be referred to as an initial state.

Figure 8:
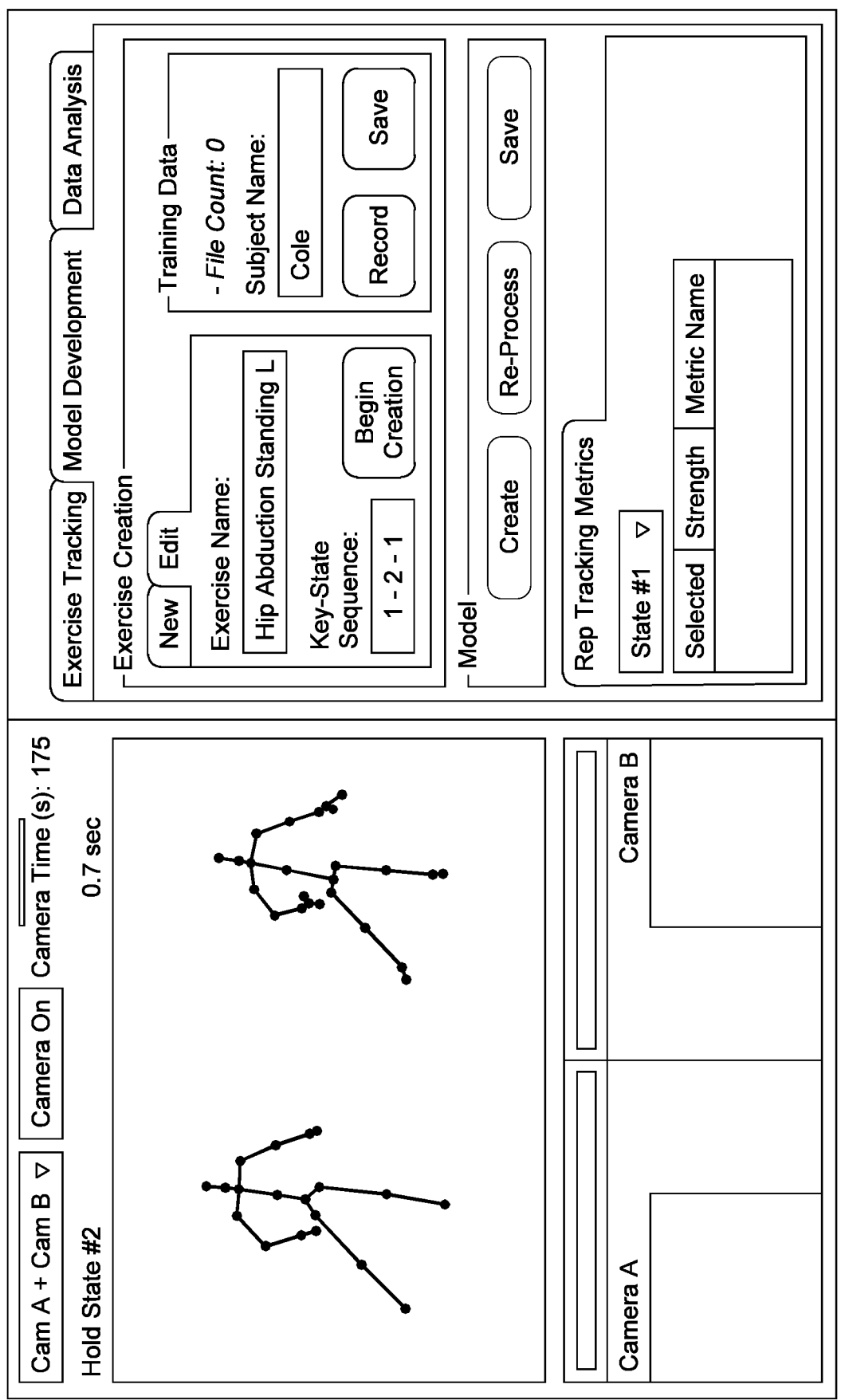
FIG. 8 depicts another view of an example user interface during a training data recording process.

FIG. 8 depicts another view of example user interface 700 in which a second state (State 2) in the defined physical activity state sequence is being demonstrated.

FIG. 9 depicts a portion 900 of user interface 700 (depicted in FIGS. 7 and 8) in which various state characteristic metrics are displayed.

In particular, the set of state characteristics metrics 902 is displayed in order of statistical strength (e.g., significance) 904 for identifying State 1. Further, a subset of the set of state characteristics is selected 906 for use in repetition tracking.

In some embodiments, the selection of state characteristic metrics may be performed automatically initially based on criteria, such as individual significance thresholds or cumulative significance for of the most significant state characteristic metrics. However, a user may further modify the selection of the state characteristic metrics using this user interface.

Figure 10:
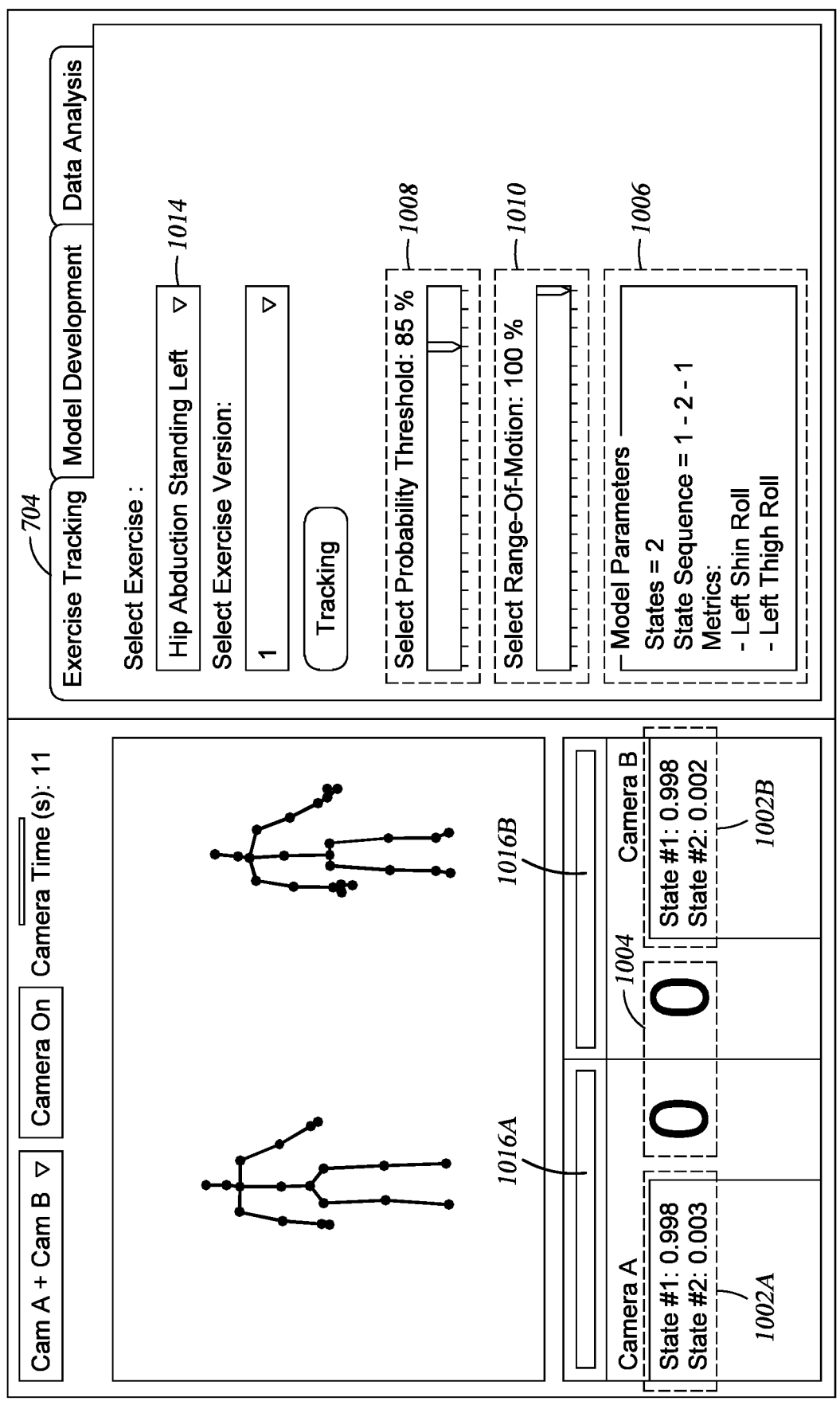
FIG. 10 depicts an example graphical user interface in an activity tracking mode.

Example Graphical User Interfaces for Tracking Motion Data Using a Physical Activity Model FIG. 10 depicts the graphical user interface 700 from FIGS. 7 and 8 in an activity tracking mode. The activity tracking mode is selected in this example via mode tab 704.

As depicted, motion data regarding a subject is being captured by two different motion tracking systems simultaneously. For each system, a physical activity model is outputting state probabilities 1002A and 1002B, which may also be referred to as classifier confidence levels, for all of the states defined as part of the physical activity being monitored. In this example, the physical activity being monitored is a "Hip Abduction Standing Left", which is shown selected in user interface element 1014. Notably, in this example, the probabilities 1002A and 1002B are slightly different based on the two different motion tracking systems. However, for both models, the probability of State 1 (as was defined in training in FIG. 7) being performed by the subject based on the captured motion data is nearly 1, i.e., the physical activity model is nearly certain that State 1 is being performed by the subject.

In this embodiment, user interface 700 includes a probability threshold adjustment user interface element 1008, which sets the threshold above which a state is determined based on the probability outputs 1002A and 1002B. In this case, the threshold is set at 85%, which means the State 1 probabilities of 0.998 pass the threshold test and the State 2 probabilities of 0.003 and 0.002 do not pass the threshold test. In this example, each camera's state tracking probability is compared independently to the threshold, but in other embodiments, each camera's state tracking probability may be averaged for a single determination.

Further in this embodiment, user interface 700 includes a range of motion adjustment user interface element 1010, through which model parameterization is performed to easily tune the model. By adjusting the range of motion, the model classifier formulas (e.g. regression coefficients) are scaled to track activities with varying ranges of motion, all from using the same training dataset.

Further in this embodiment, user interface 700 includes repetition count user interface elements 1004 (one for each of the current motion tracking systems), which count the repetitions of the physical activity. In this case, because no repetitions have been completed, each count is at 0.

Further in this embodiment, user interface 700 includes a model parameters user interface element 1006, which depicts characteristics of the current physical activity model, including the number of key states, the temporal sequence of the key states, and the state characteristic metrics used to identify the key states in captured motion data.

Figure 11:
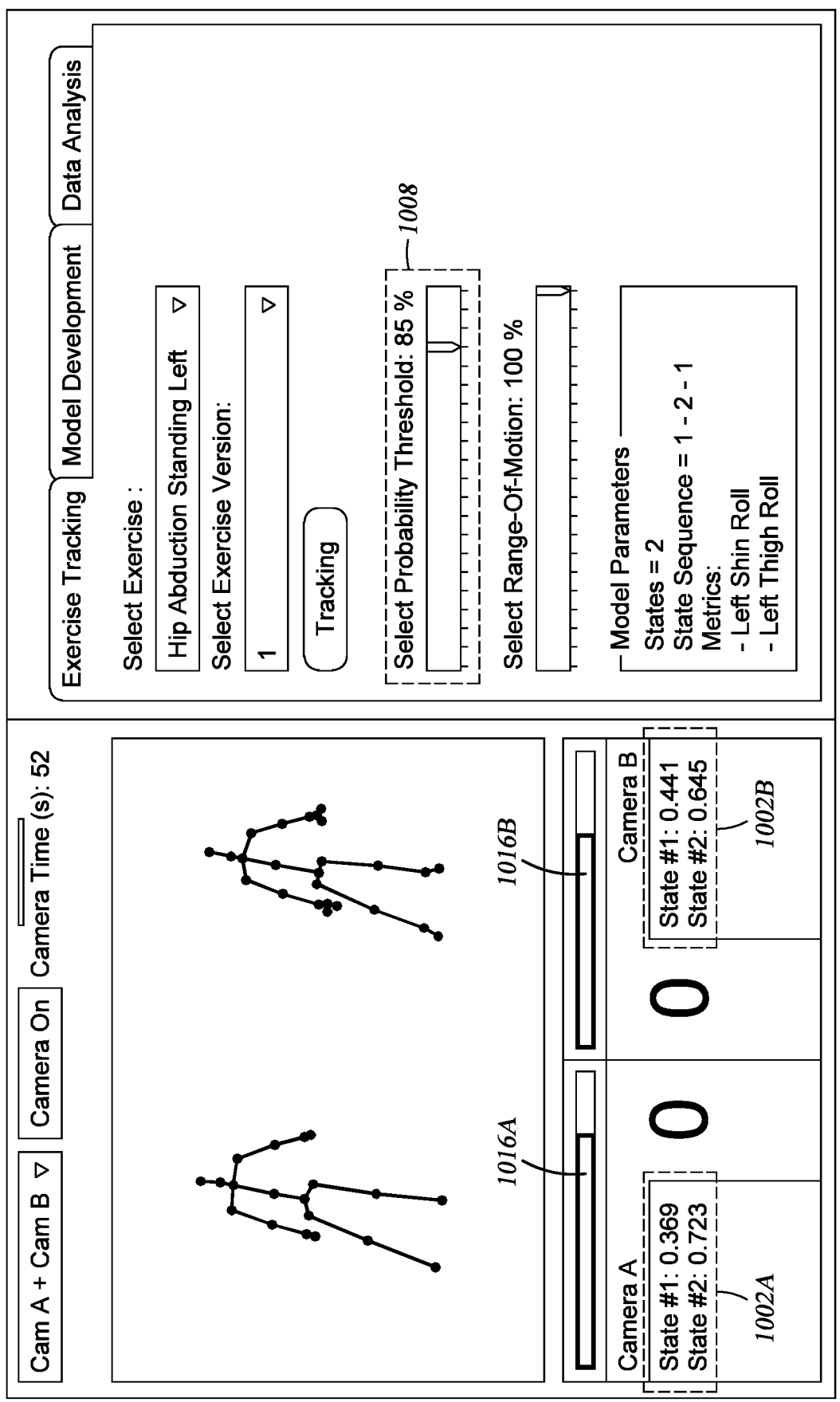
FIG. 11 depicts another view of an example graphical user interface in an activity tracking mode.

FIG. 11 depicts another view of the graphical user interface 700 from FIGS. 7 and 8 in an activity tracking mode.

As depicted, the subject has begun to transition from State 1 to State 2 (as defined above in FIG. 8). Thus, the state classifier probabilities 1002A and 1002B have changed in favor of State 2, but they have not yet exceeded the probability threshold of 0.85, as set by user interface element 1008.

Further, progress indicator bars 1016A and 1016B indicate how close the subject is to performing the current target state (State 2) with respect to the selected probability threshold, indicated at 1008.

Figure 12:
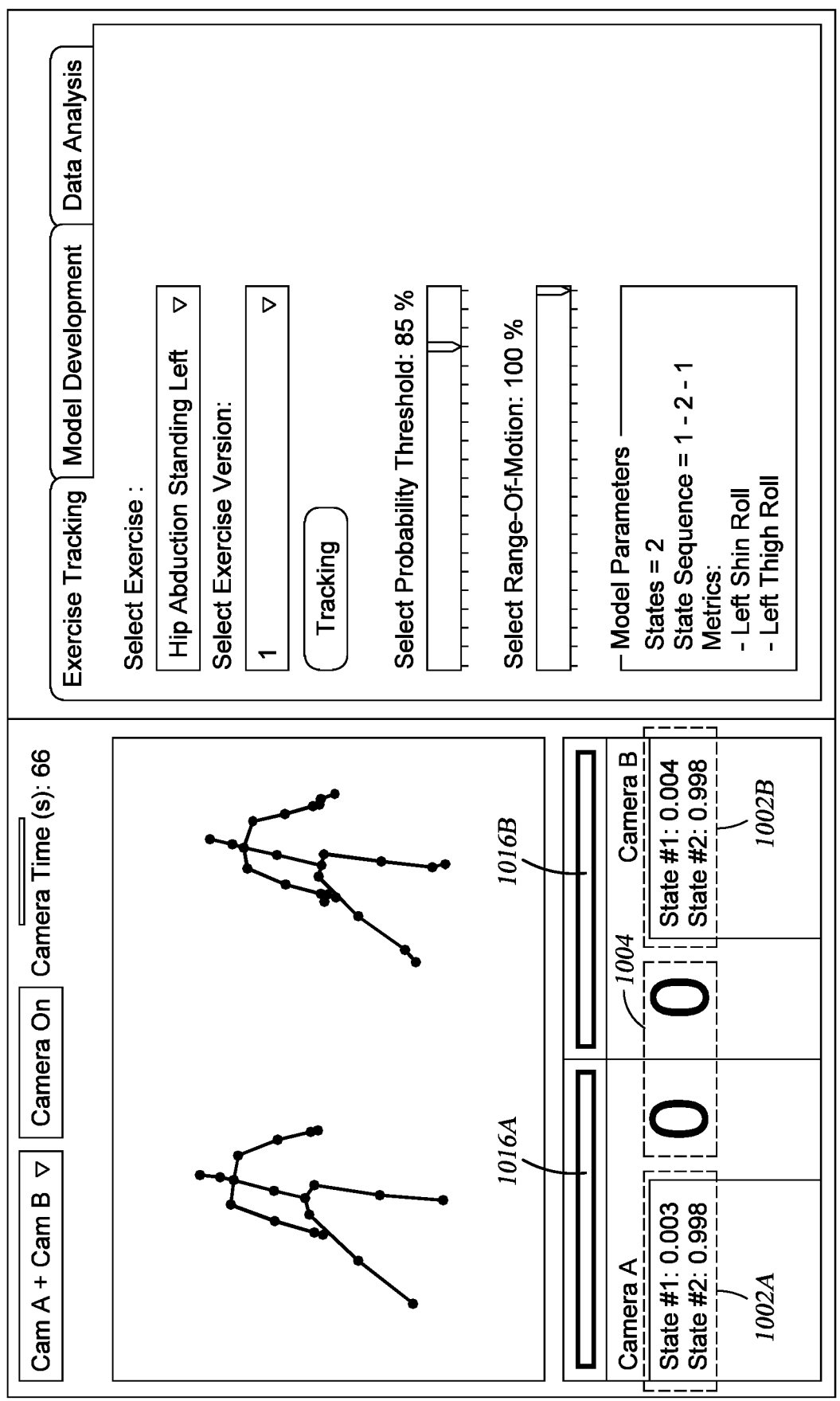
FIG. 12 depicts another view of an example graphical user interface in an activity tracking mode.

FIG. 12 depicts another view of the graphical user interface 700 from FIGS. 7 and 8 in an activity tracking mode.

As depicted, the subject has reached State 2 (as defined above in FIG. 8), and the state classifier probabilities 1002A and 1002B for State 2 now exceed the probability threshold of 0.85, as set by user interface element 1008. Consequently, the progress indicator bars 1016A and 1016B have now changed in appearance (in this example their color has changed) to indicate that State 2 has been reached based on the selected probability threshold.

Further, repetition counters 1004 now indicate one repetition has been completed because the subject has successfully performed the physical activity sequence from State 1 to State 2.

Example Method for Generating a Physical Activity Model

Figure 13:
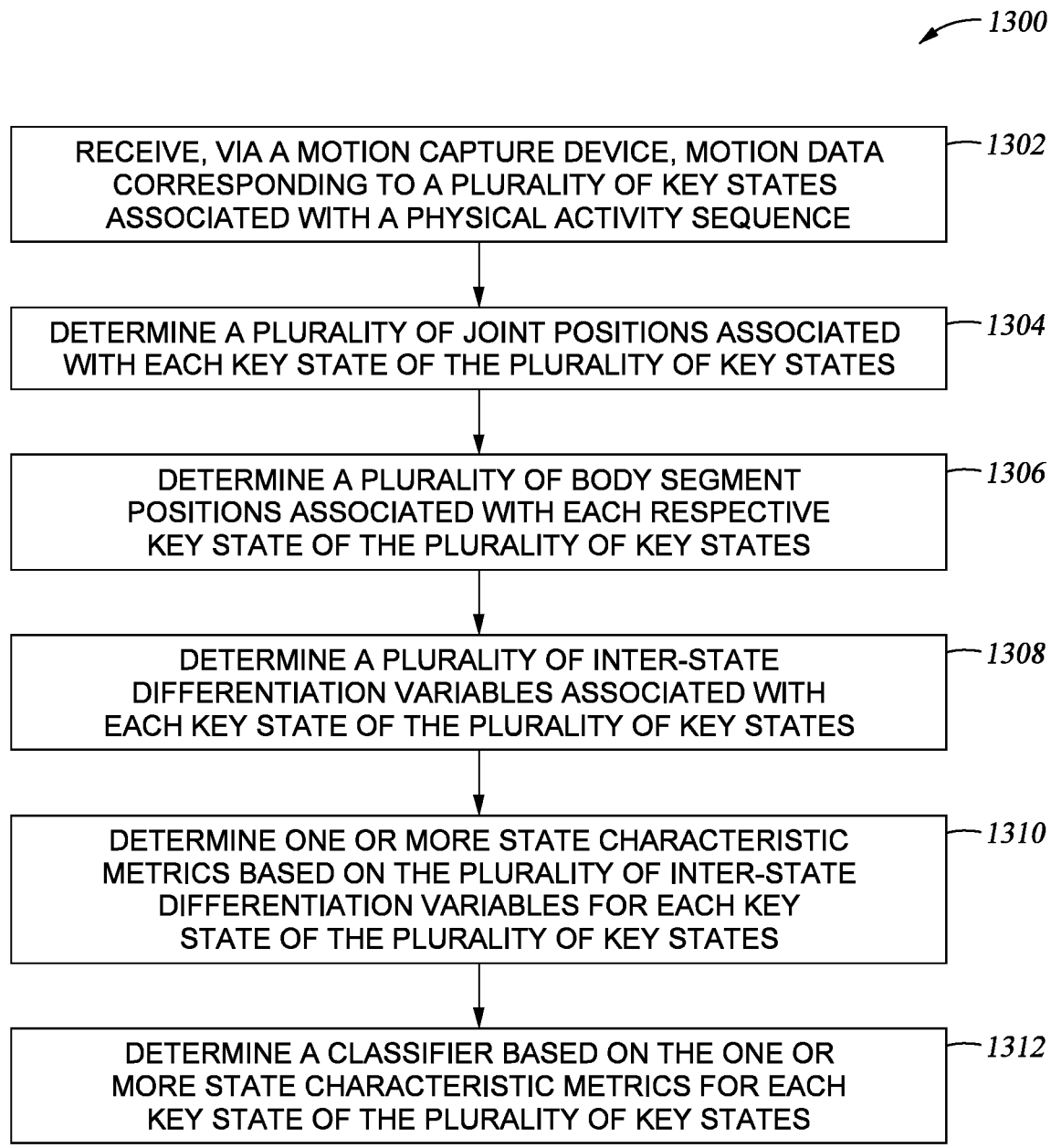
FIG. 13 depicts an example method for training a physical activity model.

FIG. 13 depicts an example method 1300 for generating a physical activity model.

Method 1300 beings at step 1302 with receiving, via a motion capture device, motion data corresponding to a plurality of key states associated with a physical activity sequence. As above, motion data may include static pose data as well as dynamic motion data, all captured by the motion capture device.

Method 1300 then proceeds to step 1304 with determining a plurality of joint positions associated with each key state of the plurality of key states, for example, as described above with respect to FIGS. 1 and 2.

Method 1300 then proceeds to step 1306 with determining a plurality of body segment positions associated with each respective key state of the plurality of key states, for example, as described above with respect to FIGS. 1 and 2.

Method 1300 then proceeds to step 1308 with determining a plurality of inter-state differentiation variables associated with each key state of the plurality of key states, for example, as described above with respect to FIGS. 1, 3, and 4.

Method 1300 then proceeds to step 1310 with determining one or more state characteristic metrics based on the plurality of inter-state differentiation variables for each key state of the plurality of key states, for example, as described above with respect to FIGS. 1, 3, and 4.

Method 1300 then proceeds to step 1312 with determining a classifier based on the one or more state characteristic metrics for each key state of the plurality of key states, for example, as described above with respect to FIGS. 1 and 4.

The physical activity model can then be generated (alternatively, defined) based on the classifiers and state characteristics associated with each key state of the plurality of key states.

In some embodiments, method 1300 further comprises determining a plurality of joint angles associated with each key state of the plurality of key states, for example, as described above with respect to FIGS. 1 and 3. In some embodiments, determining each of the plurality of joint angles associated with a respective key state may be based on the plurality of body segments positions associated with the respective key state. In some embodiments, determining the plurality of inter-state differentiation variables for the respective key state is further based on the plurality of joint angles associated with the respective key state of the plurality of key states.

In some embodiments of method 1300, determining one or more state characteristic metrics based on the plurality of inter-state differentiation variables comprises using one of: a machine-learning technique; a statistical method; or a pattern recognition approach.

In some embodiments of method 1300, the classifier for each respective key state is configured to provide a score indicating a likelihood of the respective key state in the received motion data.

In some embodiments of method 1300, determining the one or more state characteristic metrics for a respective key state further comprises: receiving a selection, via a user interface of an application, of one or more state characteristic metrics.

In some embodiments of method 1300, determining the one or more state characteristic metrics for a respective key state further comprises: determining a statistical significance of each of the plurality of inter-state differentiation variables for identifying the respective key state; and selecting as the one or more state characteristic metrics a subset of the plurality of inter-state differentiation variables based on the determined statistical significance of each of the plurality of inter-state differentiation variables.

In some embodiments of method 1300, each inter-state differentiation variable in the subset of the plurality of inter-state differentiation variables has a statistical significance above a threshold value.

In some embodiments of method 1300, a sum of the statistical significance value for each of the inter-state differentiation variables in the subset of the plurality of inter-state differentiation variables exceeds a threshold value.

In some embodiments of method 1300, each respective key state of the plurality of key states associated with the physical activity sequence is defined by monitoring a subject performing the respective key state.

In some embodiments of method 1300, each respective key state of the plurality of key states associated with the physical activity sequence is defined by an automated analysis of the received motion data.

In some embodiments of method 1300, the motion data comprises a first subset of motion data associated with a first subject and a second subset of motion data associated with a second subject.

In some embodiments of method 1300, the motion capture device comprises a depth-sensing camera.

Example Method for Using a Physical Activity Model

Figure 14:
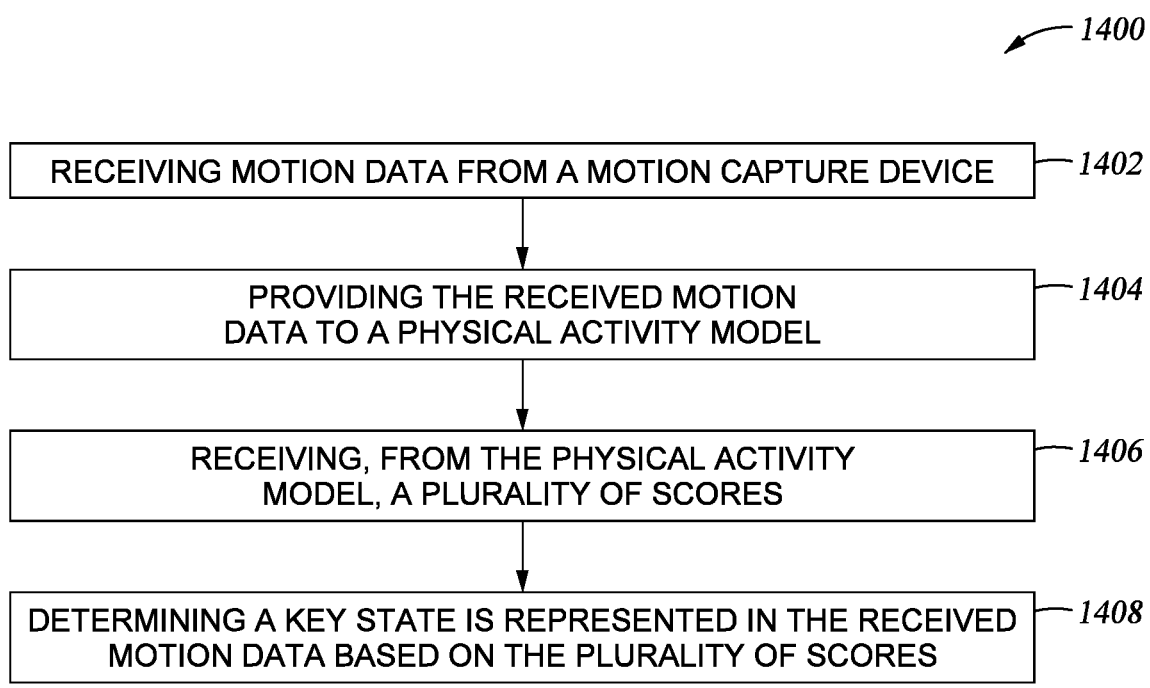
FIG. 14 depicts an example method 1400 for using a physical activity model.

FIG. 14 depicts an example method 1400 for using a physical activity model.

Method 1400 begins at step 1402 with receiving motion data from a motion capture device.

Method 1400 then proceeds to step 1404 with providing the received motion data to a physical activity model. In some embodiments of method 1400, the physical activity model comprises: a plurality of classifiers, wherein each classifier of the plurality of classifiers is associated with a key state of a physical activity; and a plurality of state characteristic metrics, wherein each state characteristic metrics of the plurality of state characteristic metrics is associated with one or more of the plurality of classifiers.

Method 1400 then proceeds to step 1406 with receiving, from the physical activity model, a plurality of scores. In some embodiments of method 1400, each score of the plurality of scores is associated with one of the plurality of classifiers.

Method 1400 then proceeds to step 1408 with determining a key state is represented in the received motion data based on the plurality of scores.

In some embodiments of method 1400, determining the key state is represented in the received motion data based on the plurality of scores further comprises: determining a score associated with the key state exceeds a threshold value.

In some embodiments of method 1400, the score associated with the key state indicates a probability that the key state is represented in the received motion data.

In some embodiments, method 1400 further comprises displaying the plurality of scores in a graphical user interface on a display device.

In some embodiments, method 1400 further comprises indicating within the graphical user interface on the display device when a respective score of the plurality of scores exceeds a threshold by changing an attribute of the respective score in the graphical user interface, wherein the attribute comprises one or more of: a color of the respective score, a size of the respective score, or a format of the respective score.

In some embodiments, method 1400 further comprises incrementing a repetition count for the physical activity based on a sequence of received scores; and displaying the repetition count in a graphical user interface on a display device.

In some embodiments of method 1400, the motion capture device is a depth-sensing camera.

Example Processing System

Figure 15:
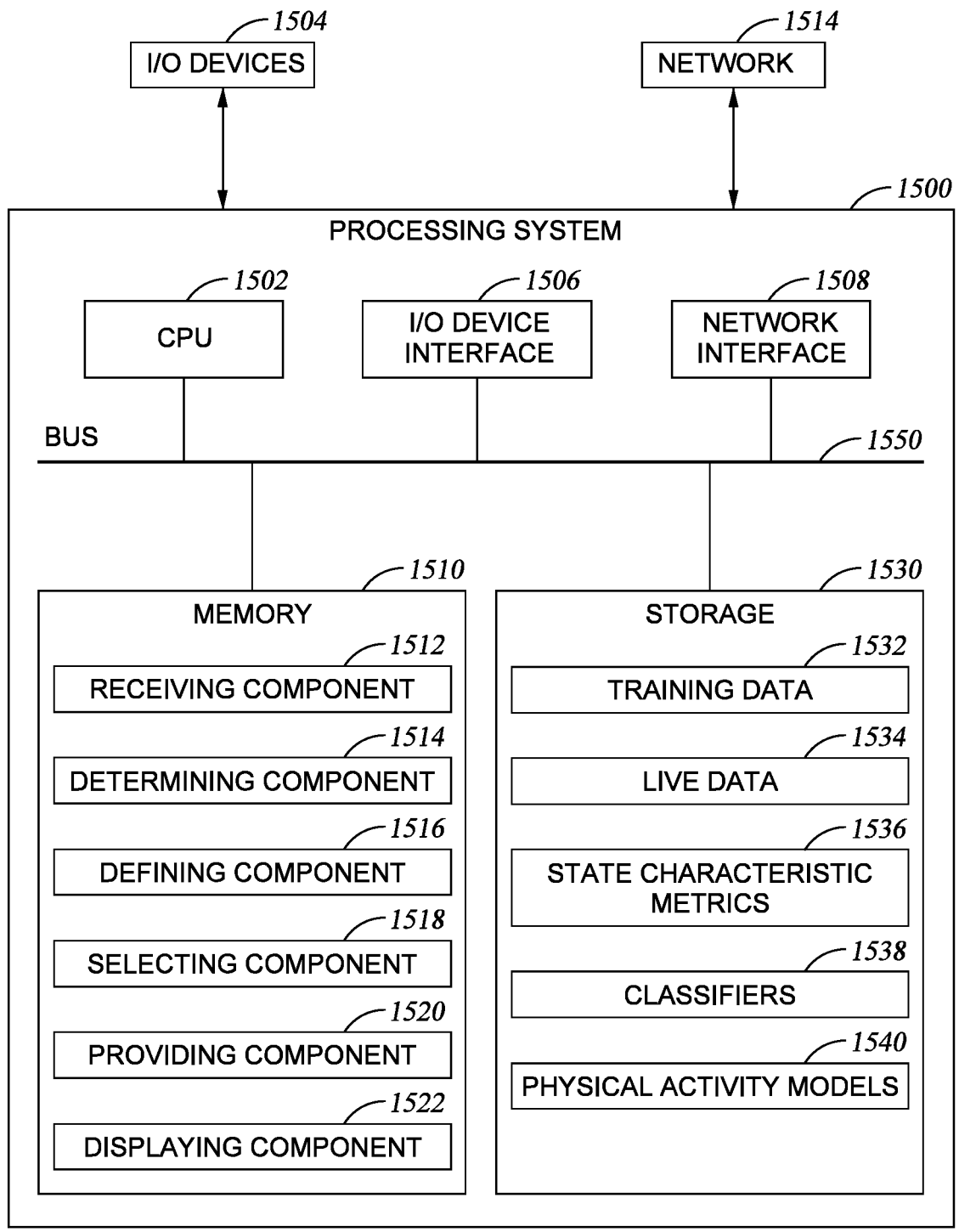
FIG. 15 depicts an example processing system 1500 configured to generate and use physical activity models.

FIG. 15 depicts an example processing system 1500 configured to generate and use physical activity models.

For example, processing system 1500 may be configured to perform one or more aspects of flow 100 described with respect to FIG. 1, flow 400 described with respect to FIG. 4, and methods 1300 and 1400 described with respect to FIGS. 13 and 14, respectively.

Processing system 1500 includes a CPU 1502 connected to a data bus 1550. CPU 1502 is configured to process computer-executable instructions, e.g., stored in memory 1510 or storage 1530, and to cause processing system 1500 to perform methods as described herein. CPU 1502 is included to be representative of a single CPU, multiple CPUs, a single CPU having multiple processing cores, and other forms of processing architecture capable of executing computer-executable instructions.

Processing system 1500 further includes input/output device(s) 1504, which may include motion capture or tracking devices as described herein, as well as input/output interface(s) 1506, which allow processing system 1500 to interface with input/output devices, such as, for example, keyboards, displays, mouse devices, pen input, motion capture or tracking devices, motion tracking sensors, and other devices that allow for interaction with processing system 1500.

Processing system 1500 further includes network interface 1508, which provides processing system 1500 with access to external networks, such as network 1514.

Processing system 1500 further includes memory 1510, which in this example includes a plurality of components.

For example, memory 1510 includes deep neural receiving component 1512, which is configured to perform receiving functions as described above, for example, with respect to methods 1300 and 1400.

Memory 1510 further includes determining component 1514, which is configured to perform determining functions as described above, for example, with respect to methods 1300 and 1400.

Memory 1510 further includes defining component 1516, which is configured to perform defining functions as described above, for example, with respect to methods 1300 and 1400.

Memory 1510 further includes selecting component 1518, which is configured to perform selecting functions as described above, for example, with respect to methods 1300 and 1400.

Memory 1510 further includes providing component 1520, which is configured to perform providing functions as described above, for example, with respect to methods 1300 and 1400.

Memory 1510 further includes displaying component 1522, which is configured to perform selecting functions as described above, for example, with respect to methods 1300 and 1400.

Note that while shown as a single memory 1510 in FIG. 15 for simplicity, the various aspects stored in memory 1510 may be stored in different physical memories, but all accessible CPU 1502 via internal data connections, such as bus 1550.

Processing system 1500 further includes storage 1530, which in this example includes training data 1532 (e.g., motion capture data for training a physical activity model), live data 1534 (e.g., live motion capture data provided to a physical activity model), state characteristic metrics 1536, classifiers 1538, and physical activity models 1540. Note that while shown as separate items for clarity, in some embodiments, a physical activity model comprises a collection of classifiers and state characteristics metrics.

While not depicted in FIG. 15, other aspects may be included in storage 1510.

As with memory 1510, a single storage 1530 is depicted in FIG. 15 for simplicity, but the various aspects stored in storage 1530 may be stored in different physical storages, but all accessible to CPU 1502 via internal data connections, such as bus 1550, or external connection, such as network interface 1508.

Notably, while shown as a single processing system in the example depicted in FIG. 15, other embodiments may include decoupled portions that function together as a processing system. For example, the various components in memory 1510 and data in storage 1530 may be implemented or stored across a network of processing systems, or in a cloud-based processing system, or in combinations of the same. For example, in some embodiments, training data 1532, physical activity models 1540, classifiers 1538, and state characteristics 1536 may be stored remote from a motion tracking system that captures live data 1534.

For example, a patient may have a client processing system that includes a motion tracking I/O device that captures lives data and feeds it back to a server processing system. Similarly, the patient's client processing system may store physical activity models 1540, classifiers 1538, and state characteristics 1536 locally, which were generated remotely, and which were downloaded to the local client processing system over a network connection, such as the Internet.

Further, processing system 1500 may be configured to function as a training system or a tracking system. Other embodiments of processing systems may be a training system only, or a tracking system only. For example, patients may receive only tracking systems.

In general, processing system 1500 is just one possible embodiment, and the various aspects of processing system 1500 may be distributed across a plurality of devices, may be omitted, or added as necessary for any of the particular functions or methods described herein.

Example Embodiments

Clause 1: A method of generating a physical activity model, comprising: receiving, via a motion capture device, motion data corresponding to a plurality of key states associated with a physical activity sequence; for each respective key state in the plurality of key states: determining a plurality of joint positions associated with the respective key state; determining a plurality of body segment positions associated with the respective key state based on the plurality of joint positions associated with the respective key state; and determining a plurality of inter-state differentiation variables for the respective key state based on one or more of: the plurality of joint positions associated with the respective key state; or the plurality of body segment positions associated with the respective key state; determining one or more state characteristic metrics for the respective key state based on the plurality of inter-state differentiation variables associated with the respective key state; and determining a classifier for the respective key state based on the one or more state characteristic metrics; and defining a physical activity model based on the one or more state characteristic metrics and the classifier associated with each key state.

Clause 2: The method of Clause 1, wherein the classifier for the respective key state is configured to provide a score indicating a likelihood of the respective key state in the received motion data.

Clause 3: The method of Clause 1 or 2, wherein determining the one or more state characteristic metrics for the respective key state further comprises: receiving a selection, via a user interface of an application, of one or more state characteristic metrics.

Clause 4: The method of any of Clauses 1-3, wherein determining the one or more state characteristic metrics for the respective key state further comprises: determining a statistical significance of each of the plurality of inter-state differentiation variables for identifying the respective key state; and selecting as the one or more state characteristic metrics a subset of the plurality of inter-state differentiation variables based on the determined statistical significance of each of the plurality of inter-state differentiation variables.

Clause 5: The method of Clause 4, wherein each inter-state differentiation variable in the subset of the plurality of inter-state differentiation variables has a statistical significance above a threshold value.

Clause 6: The method of Clause 4, wherein a sum of the statistical significance value for each of the inter-state differentiation variables in the subset of the plurality of inter-state differentiation variables exceeds a threshold value.

Clause 7: The method of any of Clauses 1-6, further comprising: determining a plurality of joint angles associated with the respective key state based on the plurality of body segments positions associated with the respective key state, wherein determining the plurality of inter-state differentiation variables for the respective key state is further based on the plurality of joint angles associated with the respective key state of the plurality of key states.

Clause 8: The method of any of Clauses 1-7, wherein each respective key state of the plurality of key states associated with the physical activity sequence is defined by monitoring a subject performing the respective key state.

Clause 9: The method of any of Clause 1-8, wherein the motion data comprises a first subset of motion data associated with a first subject and a second subset of motion data associated with a second subject.

Clause 10: The method of any of Clauses 1-9, wherein the motion capture device comprises a depth-sensing camera.

Clause 11: A processing system, comprising: a non-transitory computer-readable medium comprising computer-executable instructions; and a processor configured to execute the computer-executable instructions and cause the processing system to perform a method of generating a physical activity model, the method comprising: receiving, via a motion capture device, motion data corresponding to a plurality of key states associated with a physical activity sequence; for each respective key state in the plurality of key states: determining a plurality of joint positions associated with the respective key state; determining a plurality of body segment positions associated with the respective key state based on the plurality of joint positions associated with the respective key state; and determining a plurality of joint angles associated with the respective key state based on the plurality of body segments positions associated with the respective key state; determining a plurality of inter-state differentiation variables for the respective key state based on one or more of: the plurality of joint positions associated with the respective key state; or the plurality of body segment positions associated with the respective key state; determining one or more state characteristic metrics for the respective key state based on the plurality of inter-state differentiation variables associated with the respective key state; and determining a classifier for the respective key state based on the one or more state characteristic metrics; and defining a physical activity model based on the one or more state characteristic metrics and the classifier associated with each key state.

Clause 12: The processing system of Clause 11, wherein the classifier for the respective key state is configured to provide a score indicating a likelihood of the respective key state in the received motion data.

Clause 13: The processing system of any of Clauses 11 or 12, wherein determining the one or more state characteristic metrics for the respective key state further comprises: receiving a selection, via a user interface of an application, of one or more state characteristic metrics.

Clause 14: The processing system of any of Clauses 11-13, wherein the method further comprises: determining a plurality of joint angles associated with the respective key state based on the plurality of body segments positions associated with the respective key state, wherein determining the plurality of inter-state differentiation variables for the respective key state is further based on the plurality of joint angles associated with the respective key state of the plurality of key states.

Clause 15: A method for using a physical activity model, comprising: receiving motion data from a motion capture device; providing the received motion data to a physical activity model, wherein the physical activity model comprises: a plurality of classifiers, wherein each classifier of the plurality of classifiers is associated with a key state of a physical activity; and a plurality of state characteristic metrics, wherein each state characteristic metrics of the plurality of state characteristic metrics is associated with one or more of the plurality of classifiers; receiving, from the physical activity model, a plurality of scores, wherein each score of the plurality of scores is associated with one of the plurality of classifiers; and determining a key state is represented in the received motion data based on the plurality of scores.

Clause 16: The method of Clause 15, wherein determining the key state is represented in the received motion data based on the plurality of scores further comprises: determining a score associated with the key state exceeds a threshold value.

Clause 17: The method of Clause 16, wherein the score associated with the key state indicates a probability that the key state is represented in the received motion data.

Clause 18: The method of any of Clauses 15-17, further comprising: displaying the plurality of scores in a graphical user interface on a display device.

Clause 19: The method of Clause 18, further comprising: indicating within the graphical user interface on the display device when a respective score of the plurality of scores exceeds a threshold by changing an attribute of the respective score in the graphical user interface, wherein the attribute comprises one or more of: a color of the respective score, a size of the respective score, or a format of the respective score.

Clause 20: The method of any of Clauses 15-19, further comprising: incrementing a repetition count for the physical activity based on a sequence of received scores; and displaying the repetition count in a graphical user interface on a display device.

Clause 21: The method of any of Clauses 15-20, wherein the motion capture device is a depth-sensing camera.

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method of generating a physical activity model, comprising:
   receiving, via a motion capture device, training motion data of a user performing a physical activity sequence;
   determining a sequence of a plurality of key states in the motion data, the plurality of key states comprising a subset of states of the physical activity sequence, each of the plurality of key states comprising a specific state that in-part defines the physical activity sequence;
   for each respective key state in the plurality of key states:

determining a plurality of joint positions associated with the respective key state;

determining a plurality of body segment positions associated with the respective key state based on the plurality of joint positions associated with the respective key state; and determining a plurality of inter-state differentiation variables for the respective key state based on one or more of the plurality of joint positions associated with the respective key state or the plurality of body segment positions associated with the respective key state, the inter-state differentiation variables comprising variables used to differentiate between the plurality of key states;

determining one or more state characteristic metrics for the respective key state, the one or more state characteristic metrics comprising a subset of the plurality of inter-state differentiation variables configured to identify the respective key state; and determining a classifier for the respective key state based on the one or more state characteristic metrics, the classifier configured to determine a probability that one of the plurality of key states is in captured motion data; and defining the physical activity model based on the one or more state characteristic metrics and the classifier associated with each of the plurality of key states.

2. The method of claim 1, wherein the classifier for the respective key state is configured to provide a score indicating a likelihood of the respective key state being in the captured motion data.

3. The method of claim 1, wherein determining the one or more state characteristic metrics for the respective key state further comprises: receiving a selection, via a user interface of an application, of one or more state characteristic metrics.

4. The method of claim 1, wherein determining the one or more state characteristic metrics for the respective key state further comprises:

determining a statistical significance of each of the plurality of inter-state differentiation variables for identifying the respective key state; and selecting as the one or more state characteristic metrics a subset of the plurality of inter-state differentiation variables based on the determined statistical significance of each of the plurality of inter-state differentiation variables.

5. The method of claim 4, wherein each inter-state differentiation variable in the subset of the plurality of inter-state differentiation variables has a statistical significance above a threshold value.

6. The method of claim 4, wherein a sum of the statistical significance value for each of the inter-state differentiation variables in the subset of the plurality of inter-state differentiation variables exceeds a threshold value.

7. The method of claim 1, further comprising:

determining a plurality of joint angles associated with the respective key state based on the plurality of body segments positions associated with the respective key state, wherein determining the plurality of inter-state differentiation variables for the respective key state is further based on the plurality of joint angles associated with the respective key state of the plurality of key states.

8. The method of claim 1, wherein each respective key state of the plurality of key states associated with the physical activity sequence is defined by monitoring a subject performing the respective key state.

9. The method of claim 1, wherein the training motion data comprises a first subset of motion data associated with a first subject and a second subset of motion data associated with a second subject.

10. A processing system, comprising:

a non-transitory computer-readable medium comprising computer-executable instructions; and a processor configured to execute the computer-executable instructions and cause the processing system to perform a method of generating a physical activity model, the method comprising:

receiving, via a motion capture device, training motion data of a user performing a physical activity sequence;

determining a sequence of a plurality of key states in the motion data, the plurality of key states comprising a subset of states of the physical activity sequence, each of the plurality of key states comprising a specific state that in-part defines the physical activity sequence;

for each respective key state in the plurality of key states:

determining a plurality of joint positions associated with the respective key state;

determining a plurality of body segment positions associated with the respective key state based on the plurality of joint positions associated with the respective key state; and determining a plurality of inter-state differentiation variables for the respective key state based on one or more of the plurality of joint positions associated with the respective key state or the plurality of body segment positions associated with the respective key state, the inter-state differentiation variables comprising variables used to differentiate between the plurality of key states;

determining one or more state characteristic metrics for the respective key state, the one or more state characteristic metrics comprising a subset of the plurality of inter-state differentiation variables configured to identify the respective key state; and determining a classifier for the respective key state based on the one or more state characteristic metrics, the classifier configured to determine a probability that one of the plurality of key states is in captured motion data; and defining the physical activity model based on the one or more state characteristic metrics and the classifier associated with each of the plurality of key states.

11. The processing system of claim 10, wherein the classifier for the respective key state is configured to provide a score indicating a likelihood of the respective key state being in the captured motion data.

12. The processing system of claim 10, wherein determining the one or more state characteristic metrics for the respective key state further comprises: receiving a selection, via a user interface of an application, of one or more state characteristic metrics.

13. The processing system of claim 10, wherein the method further comprises:

determining a plurality of joint angles associated with the respective key state based on the plurality of body segments positions associated with the respective key state, wherein determining the plurality of inter-state differentiation variables for the respective key state is further based on the plurality of joint angles associated with the respective key state of the plurality of key states.

14. A method of analyzing user motion using a physical activity model associated with a physical activity sequence, comprising:
   receiving motion data from a motion capture device of a user performing the physical activity sequence;
   providing the received motion data to a physical activity model, wherein the physical activity model comprises:
      a plurality of classifiers, wherein each classifier of the plurality of classifiers is associated with a key state of the physical activity sequence, the key state comprising a specific state that, in-part with a plurality of key states, defines the physical activity sequence; and
      a plurality of state characteristic metrics, wherein each of the plurality of state characteristic metrics is associated with one or more of the plurality of classifiers, the plurality of state characteristic metrics comprising a subset of a plurality of inter-state differentiation variables configured to identify the respective key state;
   receiving, from the physical activity model, a plurality of scores, wherein each score of the plurality of scores is associated with one of the plurality of classifiers; and
   determining that the key state is represented in the received motion data based on the plurality of scores.

15. The method of claim 14, wherein determining the key state is represented in the received motion data based on the plurality of scores further comprises: determining a score associated with the key state exceeds a threshold value.

16. The method of claim 15, wherein the score associated with the key state indicates a probability that the key state is represented in the received motion data.

17. The method of claim 14, further comprising:
   indicating via a graphical user interface on the display device when a respective score of the plurality of scores exceeds a threshold by changing an attribute of the respective score in the graphical user interface,
   wherein the attribute comprises one or more of: a color of the respective score, a size of the respective score, or a format of the respective score.

18. The method of claim 14, further comprising: incrementing a repetition count for the physical activity based on a sequence of received scores; and
   displaying the repetition count in a graphical user interface on a display device.

19. The method of claim 1, comprising:
   receiving range of motion adjustment input indicating a range of motion value; and
   scaling the classifier to track activity based on the range of motion value.

20. The processing system of claim 10, wherein the method further comprises:
   receiving range of motion adjustment input indicating a range of motion value; and
   scaling the classifier to track activity based on the range of motion value.

21. The method of claim 14, comprising determining, via the physical activity model, a prediction of risk of potential injury based on the received motion data.

* * * * *